(12) United States Patent
Chow et al.

(10) Patent No.: US 8,216,852 B2
(45) Date of Patent: Jul. 10, 2012

(54) CHANNEL CROSS-SECTION GEOMETRY TO MANIPULATE DISPERSION RATES

(75) Inventors: Andrea W. Chow, Los Altos, CA (US); H. Garrett Wada, Atherton, CA (US)

(73) Assignee: Caliper Life Sciences, Inc., Alameda, CA (US)

(*) Notice: Subject to any disclaimer, the term of this patent is extended or adjusted under 35 U.S.C. 154(b) by 0 days.

(21) Appl. No.: 12/947,963

(22) Filed: Nov. 17, 2010

(65) Prior Publication Data

US 2011/0063943 A1 Mar. 17, 2011

Related U.S. Application Data

(63) Continuation of application No. 11/268,952, filed on Nov. 7, 2005, now abandoned, which is a continuation of application No. 10/206,787, filed on Jul. 26, 2002, now abandoned.

(60) Provisional application No. 60/308,368, filed on Jul. 27, 2001.

(51) Int. Cl.
   *G01N 1/00* (2006.01)
(52) U.S. Cl. ............ 436/174; 422/73; 422/81; 422/50; 422/500; 422/501; 436/180
(58) Field of Classification Search ............ 422/73, 422/81, 50, 500–501; 436/180, 174
See application file for complete search history.

(56) References Cited

U.S. PATENT DOCUMENTS

| | | | |
|---|---|---|---|
| 4,756,884 A | 7/1988 | Hillman et al. | |
| 5,271,724 A | 12/1993 | van Lintel | |
| 5,277,566 A | 1/1994 | Augustin et al. | |
| 5,375,979 A | 12/1994 | Trah | |
| 5,635,358 A * | 6/1997 | Wilding et al. | ............ 435/7.2 |
| 5,705,018 A | 1/1998 | Hartley | |
| 5,792,943 A | 8/1998 | Craig | |
| 5,800,690 A | 9/1998 | Chow et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,942,443 A | 8/1999 | Parce et al. | |
| 5,965,410 A | 10/1999 | Chow et al. | |
| 5,985,217 A | 11/1999 | Krulevitch et al. | |
| 6,001,231 A | 12/1999 | Kopf-Sill | |
| 6,100,541 A | 8/2000 | Nagle et al. | |
| 6,150,119 A | 11/2000 | Kopf-Sill et al. | |
| 6,174,675 B1 | 1/2001 | Chow et al. | |

(Continued)

FOREIGN PATENT DOCUMENTS

WO 9405414 3/1994

(Continued)

OTHER PUBLICATIONS

Aris, R., "On the Dispersion of a Solute in a Fluid Flowing Through a Tube," Proc. Roy. Soc. (1956) 235:67-77.

(Continued)

*Primary Examiner* — Jyoti Nagpaul
(74) *Attorney, Agent, or Firm* — Cardinal Law Group

(57) ABSTRACT

The present invention provides novel methods for controlling/manipulating materials flowing in a fluidic device. In particular, the methods of the invention create and utilize differences between dispersion rates and/or average velocity of materials in order to manipulate the materials.

17 Claims, 7 Drawing Sheets

U.S. PATENT DOCUMENTS

| | | | |
|---|---|---|---|
| 6,416,642 | B1 | 7/2002 | Alajoki et al. |
| 6,458,259 | B1 | 10/2002 | Parce et al. |

FOREIGN PATENT DOCUMENTS

| | | |
|---|---|---|
| WO | 9604547 | 2/1996 |
| WO | 9702357 | 1/1997 |
| WO | 9800231 | 1/1998 |
| WO | 9800705 | 1/1998 |
| WO | 9845481 | 10/1998 |
| WO | 9846438 | 10/1998 |
| WO | 9849548 | 11/1998 |
| WO | 0070080 | 11/2000 |

OTHER PUBLICATIONS

Aris, R., "On the Dispersion of a Solute in a Fluid Flowing Through a Tube," Proc. Roy. Soc. (1956) 235:67-77.

Chatwin, P.C. et al., "The Effect of Aspect Ratio on Longitudinal Diffusivity in Rectangular Channels," J.Fluid Mech. (1982) 120:347-358.

Doshi, M.R. et al., "Three Dimensional Laminar Dispersion in Open and Closed Rectangular Conduits," Chem. Eng. Science (1978) 33:795-804.

Guell, D.C. et al., "Taylor Dispersion in Conduits of Large Aspect Ratio," Chem. Eng. Comm. (1987) 58:231-244.

Kopp, M.U. et al., "Chemical Amplification: Continuous-Flow PCR on a Chip," Science (1998) 280:1046-1048.

Taylor, G., "Dispersion of Soluble Matter in Solvent Flowing Slowly Through a Tube," Proc. Roy. Soc. (1953) 219A:186-203.

Dutta, D., et al., "Dispersion Reduction in Pressure-Driven Flow Through Microetched Channels," Anal. Chem. (2001) 73:504-513.

\* cited by examiner

-0.25 psi, 1/50 beads, 0.5 μM fluorescein in Cell Buffer + 0.1% BSA NS74-50 μm cap.

Anti-MHC-II alone, no cells, 1/50 dilution

CHANNEL CROSS-SECTION GEOMETRY TO MANIPULATE DISPERSION RATES

CROSS-REFERENCE TO RELATED APPLICATIONS

This application is a continuation of U.S. patent application Ser. No. 11/268,952, filed Nov. 7, 2005, which is a continuation of U.S. patent application Ser. No. 10/206,787, filed Jul. 26, 2002, which claims the benefit of U.S. Provisional Patent Application No. 60/308,368, filed Jul. 27, 2001, all of which are incorporated herein by reference in their entirety for all purposes.

BACKGROUND OF THE INVENTION

When carrying out chemical or biochemical analyses, assays, syntheses or preparations, a large number of separate manipulations are performed on the material(s) or component(s) to be assayed, including measuring, aliquotting, transferring, diluting, mixing, separating, detecting, incubating, etc. Microfluidic technology miniaturizes these manipulations and integrates them so that they can be executed within one or a few microfluidic devices. For example, pioneering microfluidic methods of performing biological assays in microfluidic systems have been developed, such as those described by Parce et al., "High Throughput Screening Assay Systems in Microscale Fluidic Devices" U.S. Pat. No. 5,942,443 and Knapp et al., "Closed Loop Biochemical Analyzers" (WO 98/45481).

Of particular interest in numerous applications utilizing microfluidic devices is the movement/transport of, e.g., samples, reagents, analytes, etc. often in discrete bands (or plugs). For example, in many experimental/assay situations it is desirous to keep plugs of different samples (e.g., a selection of possible enzymatic inhibitors) from diffusing or dispersing into one another as the samples are flowed through various regions of a microfluidic device. This is especially true in high throughput systems where muddying or intermingling of sample plugs can severely decrease throughput efficiency.

Conversely, it is also of interest in the use of microfluidic devices to move/transport fluidic materials (e.g., samples, reagents, analytes, etc.) in such a way as to, e.g., separate multiple materials from within a single plug into various separate plugs and/or to "stretch" a particular sample plug into a longer, and therefore, e.g., less concentrated, length.

The amount/degree of dispersion of samples, etc. in microfluidic devices is influenced by how the samples, etc. are transported through the microfluidic device. Fluidic materials (e.g., in sample plugs) are transported through microfluidic devices in numerous ways using, e.g., electrokinetic flows (electrophoresis or electroosmosis), pressure (e.g., via application of a positive force or via a vacuum), hydrostatic forces, etc. However, various flow regimens used in microfluidic devices can lead to dispersion of plugs of fluid material in the microfluidic elements (e.g., microchannels). For example, pressure driven flow can result in sometimes large amounts of Taylor dispersion of a fluidic material. Additionally, even electroosmotic flow and hydrostatic flow can cause small pressure gradients along a microchannel due to, e.g., mismatch of electroosmotic flow rates, etc. Such can lead to, e.g., dispersion even when fluidic materials are transported via electrokinetic methods.

A welcome addition to the art would be the ability to manipulate the length of sample plugs (e.g., to minimize lengthening [i.e., to keep plugs intact] and/or to maximize lengthening [i.e., to separate mixed samples or to dilute samples]) as the plugs are flowed through a microfluidic device. The current invention describes and provides these and other features by providing new methods, microchannels, and microfluidic devices that meet these and other goals.

SUMMARY OF THE INVENTION

The present invention provides methods, systems, microchannels, kits, and devices for controlling and manipulating aliquots of fluidic materials in microfluidic devices. Fluidic materials are flowed through microfluidic devices comprising microchannels of "regular" cross-sectional geometry and/or "specifically configured" cross-sectional geometry. The invention utilizes differences in dispersion rates and/or average velocities of the fluidic materials created by the particular cross-sectional geometry of the channels in which the fluidic materials are flowed.

In one aspect, the invention comprises an integrated system or microfluidic device having a body structure with at least one microchannel with a cross-sectional geometry configured to manipulate a dispersion rate and/or an average velocity of at least one fluidic material. Such integrated system or microfluidic device further has one or more detection regions of the microchannel; a source(s) of one or more fluidic materials coupled to the microchannel; fluid direction systems and a detection system proximal to the detection region. Such microchannel in the system or device optionally has a cross-sectional geometry that manipulates the dispersion rate and/or the average velocity of the fluidic material relative to the dispersion rate and/or average velocity of the same fluidic material in a microchannel having a substantially rectangular cross-sectional geometry. In some embodiments, at least 2 fluidic materials each having a dispersion rate and/or each having an average velocity are flowed through the system/device. The cross-sectional geometry of the microchannel optionally manipulates the dispersion rates and/or average velocities of such fluidic materials to either be the same and/or to be different rates/velocities (e.g., 1.25, 1.5, 1.75, 2, 3, 4, 5, or 10 times different, i.e., the dispersion rate and/or average velocity of one fluidic material is 1.25, etc. times greater than the other).

In other aspects, the invention comprises a method of manipulating a dispersion rate and/or average velocity of a fluidic material in an integrated system or microfluidic device by flowing the material through a microchannel whose cross-sectional geometry is configured to manipulate the dispersion rate and/or average velocity relative to the dispersion rate and/or average velocity of the same fluidic material in a microchannel of substantially rectangular cross-sectional geometry. In some embodiments, such method includes flowing at least 2 fluidic materials through the microchannel, each material having a dispersion rate and/or average velocity. The cross-sectional geometry of the microchannel is optionally specifically configured to manipulate the dispersion rates and/or average velocities of the fluidic materials to either be the same and/or to be different rates/velocities (e.g., one rate/velocity being 1.25, 1.5, 1.75, 2, 3, 4, 5, or 10 times greater than the other rate/velocity). In some embodiments, the microchannels of such systems/devices change over the length of the microchannels. Also such systems/devices optionally comprise fluid direction systems using one or more of electrokinetic flow, positive pressure, negative pressure, hydrostatic pressure, or wicking forces (or a combination of such) as well as optionally comprising an operably attached computer attached to the detection system for acquiring data and tracking dispersion rates and/or average velocities of the fluidic materials.

In other aspects, the invention comprises a microchannel with one or more region whose cross-sectional geometry is configured to manipulate the dispersion rate and/or average velocity of at least one fluidic material relative to the dispersion rate and/or average velocity of the same material in a microchannel of substantially rectangular cross-sectional geometry. Such manipulation can be to increase and/or to decrease the dispersion rate and/or average velocity of the fluidic material. In some embodiments, multiple fluidic materials are flowed through the microchannel (e.g., a first fluidic material and at least a second fluidic material) each of which has a dispersion rate and/or average velocity (e.g., a first dispersion rate and/or average velocity and a second dispersion rate and/or average velocity, etc.). The cross-sectional geometry of the microchannel is specifically configured to optionally manipulate the first dispersion rate and/or average velocity to be the same as the second dispersion rate and/or average velocity or, alternatively and/or additionally, to manipulate the first dispersion rate and/or average velocity to be different than the second dispersion rate and/or average velocity. The cross-sectional geometry of the microchannel can be configured so that the first dispersion rate and/or average velocity is, e.g., 1.25, 1.5, 1.75, 2, 3, 4, 5, or 10 times greater than the second dispersion rate and/or average velocity.

In other aspects, the invention comprises a method of designing a microchannel (and/or a region(s) of a microchannel) comprising one or more region by selecting a cross-sectional geometry to manipulate the dispersion rate and/or average velocity of at least one fluidic material. Such microchannel can be of multiple regions (e.g., a first region and a second region) having different cross-sectional geometries. Such dispersion rate and/or average velocity is optionally manipulated relative to the dispersion rate and/or average velocity of the same fluidic material in a microchannel of substantially rectangular cross-sectional geometry. In some embodiments such method involves a first fluidic material (with a first dispersion rate and/or average velocity) and at least a second fluidic material (with a second dispersion rate and/or average velocity). Such method can comprise selecting a specific cross-sectional geometry of a region of the microchannel to either make the dispersion rates and/or average velocities of the two fluidic materials be the same and/or for the dispersion rates and/or average velocities to be different (e.g., the first dispersion rate and/or average velocity can be 1.25, 1.5, 1.75, 2, 3, 4, 5, or 10 times greater than the second).

In yet other aspects, the invention comprises an integrated system or microfluidic device for separating at least two fluidic materials based upon a difference in the dispersion rate and/or average velocity of the fluidic materials. Such integrated system or microfluidic device comprises a body structure with at least one microchannel that causes a first fluidic material (with a first dispersion rate and/or average velocity) to have a different dispersion rate and/or average velocity than a second fluidic material (with a second dispersion rate and/or average velocity). Furthermore, such microchannel has a detection region and does not have a separation matrix for separating the fluidic materials. Additionally, the system or device has a source of the first and second fluidic materials (both of which sources are coupled to the at least one microchannel and which optionally are the same source); a fluidic direction system to move the fluidic materials without the use of electrokinetic flow; and a detection system proximal to the detection region. In some embodiments of the system/device, the dispersion rate and/or average velocity of the first fluidic materials is 1.25, 1.5, 1.75, 2, 3, 4, 5, or 10 times greater than the dispersion rate and/or average velocity of the second fluidic material. Additionally, in some embodiments, the microchannel in such system or device changes its cross-sectional geometry over the length of the microchannel. Such system or device also has a fluidic direction system that uses one or more (or a combination of) positive pressure, negative pressure, hydrostatic forces, or wicking forces. Such system or device, furthermore, optionally has a computer operably coupled to the detector system with instructions to acquire data, track the dispersion rates and/or average velocities of the fluidic materials, etc.

In yet other aspects, the invention comprises a method of separating at least two fluidic materials in an integrated system or microfluidic device based upon differences in dispersion rate and/or average velocity of the fluidic materials. Such method comprises flowing a first fluidic material (with a corresponding first dispersion rate and/or average velocity) and at least a second fluidic material (with a corresponding second dispersion rate and/or average velocity) through a microchannel that does not have a separation matrix and wherein the flow is not via electrokinetic force. In some embodiments, such method involves flowing through microchannels whose cross-sectional geometry causes the dispersion rate and/or average velocity of the first fluidic materials to be 1.25, 1.5, 1.75, 2, 3, 4, 5, or 10 times greater than the dispersion rate and/or average velocity of the second fluidic material.

DETAILED DISCUSSION OF THE INVENTION

Figure 1:
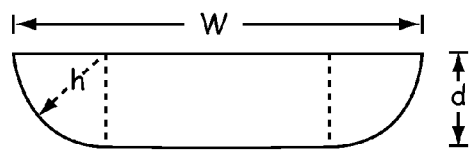
FIG. 1 is a schematic cross-view of a microchannel of regular cross-sectional geometry.

The methods and devices of the current invention directly address and solve problems associated with control and manipulation of aliquots of fluidic material in microfluidic devices. Briefly, the invention provides devices and methods for altering microchannel cross-sectional geometry in order to control dispersion and/or average velocity of various fluidic materials (e.g., in order to separate or not to separate the various fluidic materials); and separating various fluidic materials based upon their dispersion rates and/or average velocity in a "regular" cross-sectional geometry microchannel under non-electrokinetic flow.

The methods and devices of the current invention used to control and manipulate aliquots of fluidic material are flexible and can be utilized in many different embodiments of microfluidic devices which perform myriad assays, tasks, etc. The methods and devices herein can be utilized in microfluidic devices to, e.g., maximize throughput time, when such is applicable to the assay(s) being performed. For example, the screening of large libraries (or extremely large libraries, etc) such as combinatorial libraries can be time consuming due to the aggregation of time requirements for each individual assay. While microfluidic devices ease the process of such large screenings, assays that have low throughput or non-optimized throughput can still have substantial time requirements. The combination of elements that constitute the methods and devices of the current invention cleverly allow for optimizing of throughput by decreasing or eliminating intermingling and/or spreading of sample aliquots, thus substantially decreasing time requirements for assays in microfluidic devices. Furthermore, the methods and devices of the present invention allow aliquots of mixed materials to be separated into their individual components in situations which preclude use of, e.g., electrophoretic separation, separation matrices (e.g., gel matrices, etc.), etc. due to the parameters/characteristics of the particular usage.

The current invention differs from other, previous, methods and devices in numerous ways. For example, the current invention utilizes, e.g., specific alterations of microchannel cross-sectional geometry to manipulate/control dispersion and average velocity of fluidic aliquots. Additionally, the current invention utilizes differences in the dispersion rates and/or average velocity of fluidic materials in "regular" shaped microchannels to separate such materials without the use of, e.g., electrophoresis, separation matrices, etc. The combination of these elements allows for adjustment and modification of balances between the several elements of the invention in order to, e.g., optimize throughput for the specific assay(s) to be performed, allow for specific needs of particular constituents (e.g., ones that cannot be separated through separation matrices, etc.), etc.

The present invention also optionally includes various elements involved in, e.g., transporting fluidic materials involved, reconstitution of dried or immobilized samples, temperature control, fluid transport mechanisms, detection and quantification of molecular interactions (e.g., fluorescence detectors), robotic devices for, e.g., positioning of components or devices involved, etc.

METHODS AND DEVICES OF THE INVENTION

Manipulation/control of molecules, compounds, etc. in microfluidic devices is often done within one or more microchannels (sometimes referred to herein as microfluidic channels) or microreservoirs, etc. The term "microfluidic," as used herein, refers to a device component, e.g., chamber, channel, reservoir, or the like, that includes at least one cross-sectional dimension, such as depth, width, length, diameter, etc., of from about 0.1 micrometer to about 500 micrometer. Examples of microfluidic devices are detailed in, e.g., U.S. Pat. No. 5,942,443 issued Aug. 24, 1999, entitled "High Throughput Screening Assay Systems in Microscale Fluidic Devices" to J. Wallace Parce et al. and U.S. Pat. No. 5,880,071 issued Mar. 9, 1999, entitled "Electropipettor and Compensation Means for Electrophoretic Bias" to J. Wallace Parce et al., both of which are incorporated herein by reference for all purposes.

Figure 2A:
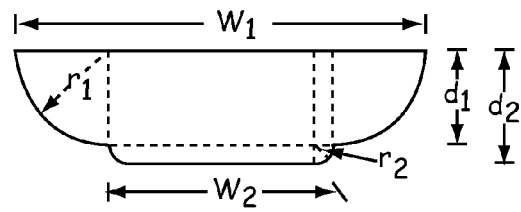
FIG. 2, panels A through H, are schematic cross-views of sample specifically configured microchannels.
Figure 2B:
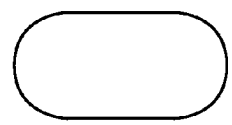

In general, microfluidic devices are planar in structure and are constructed from an aggregation of planar substrate layers wherein the fluidic elements, such as microchannels, etc., are defined by the interface of the various substrate layers. The microchannels, etc. are usually etched, embossed, molded, ablated, or otherwise fabricated into a surface of a first substrate layer as grooves, depressions, or the like. A second substrate layer is subsequently overlaid on the first substrate layer and bonded to it in order to cover the grooves, etc. in the first layer, thus creating sealed fluidic components within the interior portion of the device. Optionally, either one or both substrate layer has microchannels devised within it. Such microchannels can be aligned one on top of another when the substrate layers are joined together. Such microchannels as thus constructed can be symmetrical (i.e., the microchannel on the first substrate is the same shape as that of the microchannel on the second substrate, thus forming a symmetrical microchannel when the two substrate layers are joined, see, e.g., FIGS. 2B, E, and F) or such microchannels can be asymmetrical (i.e., the microchannel on the first substrate is a different shape from that of the microchannel on the second substrate, thus forming an asymmetrical channel when the two substrate layers are joined, see, e.g., FIGS. 2A, D, G, and H). Additionally, open-well elements can be formed by making perforations in one or more substrate layers, which perforation optionally can correspond to depressed microreservoir, microchannel, etc. areas on the complementary layer.

Manufacturing of these microscale elements into the surface of the substrates can be carried out through any number of microfabrication techniques that are well known in the art. For example, lithographic techniques are optionally employed in fabricating, e.g., glass, quartz, or silicon substrates, using methods well known in the semiconductor manufacturing industries, such as photolithographic etching, plasma etching, or wet chemical etching. Alternatively, micromachining methods such as laser drilling, micromilling, and the like are optionally employed. Similarly, for polymeric substrates, well known manufacturing techniques may also be used. These techniques include injection molding or stamp molding methods wherein large numbers of substrates are optionally produced using, e.g., rolling stamps to produce large sheets of microscale substrates, or polymer microcasting techniques where the substrate is polymerized within a micromachined mold. Furthermore, various combinations of such techniques are optionally combined to produce the microelements present in the current invention.

As stated above, the substrates used to construct the microfluidic devices of the invention are typically fabricated from any number of different materials, depending upon, e.g., the nature of the samples to be assayed, the specific reactions and/or interactions being assayed for, etc. For some applications, the substrate can optionally comprise a solid non-porous material. For example, the substrate layers can be composed of, e.g., silica-based materials (such as glass, quartz, silicon, fused silica, or the like), polymeric materials or polymer coatings on materials (such as polymethylmethacrylate, polycarbonate, polytetrafluoroethylene, polyvinylchloride, polydimethylsiloxane, polysulfone, polystyrene, polymethylpentene, polypropylene, polyethylene, polyvinylidine fluoride, acrylonitrile-butadiene-styrene copolymer, parylene or the like), ceramic materials, metal materials, etc.

The surface of a substrate layer may be of the same material as the non-surface areas of the substrate or, alternatively, the surface may comprise a coating on the substrate base. Furthermore, if the surface is coated, the coating optionally can cover either the entire substrate base or can cover select subparts of the substrate base. For example, in the case of glass substrates, the surface of the glass of the base substrate may be treated to provide surface properties that are compatible and/or beneficial to one or more sample or reagent being used. Such treatments include derivatization of the glass surface, e.g., through silanization or the like, or through coating of the surface using, e.g., a thin layer of other material such as a polymeric or metallic material. Derivatization using silane chemistry is well known to those of skill in the art and can be readily employed to add, e.g., amine, aldehyde, or other functional groups to the surface of the glass substrate, depending upon the desired surface properties. Further, in the case of metal substrates, metals that are not easily corroded under potentially high salt conditions, applied electric fields, and the like are optionally preferred.

Figure 3A:
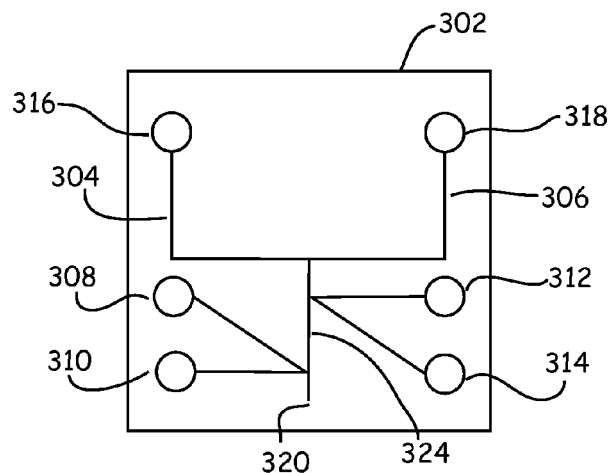
FIG. 3, panels A, B, and C, are schematic views of optional embodiments of the invention comprising microchannels of various cross-sectional geometries.
Figure 3B:
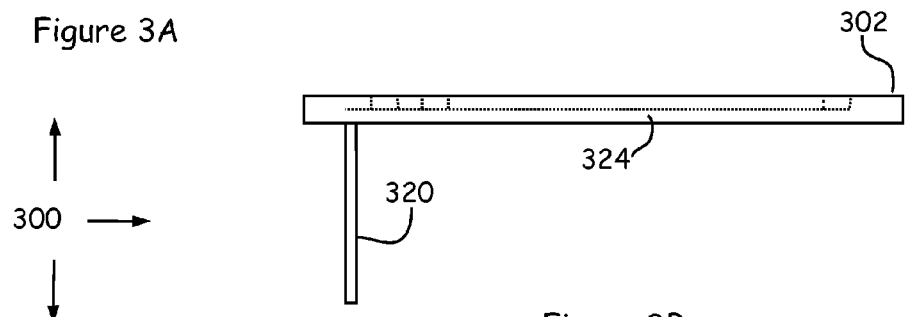
Figure 3C:
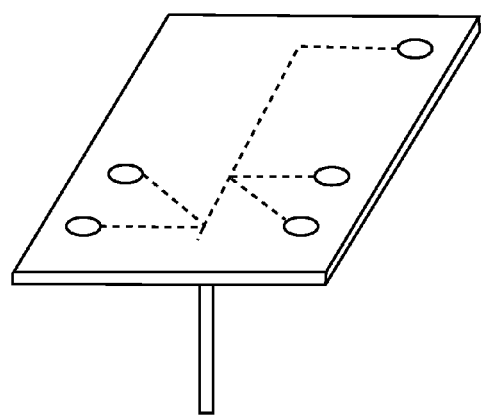

Although described in terms of a layered planar body structure, it will be appreciated that microfluidic devices in general and the present invention in particular can take a variety of forms, including aggregations of various fluidic components such as capillary tubes, individual chambers, arrangement of channel(s) etc., that are pieced together to provide the integrated elements of the complete device. For example, FIG. 3, panels A, B, and C, illustrates one of many possible arrangements of the elements of the present invention. In one such possible arrangement, as shown in FIG. 3, body structure 302 has main channels 304 and 306 disposed therein, which are fluidly connected to various reservoirs that can optionally contain, e.g., buffer, reagents, etc. Channel 304 as presented in FIG. 3 comprises a microchannel whose cross-sectional geometry has been specifically configured to manipulate the dispersion rate and/or average velocity of one or more fluidic material flowed through the microchannel. Alternatively, only a sub-portion or sub-region of channel 304 is so configured. Channel 306 as presented in FIG. 3 comprises a microchannel of "regular" shape, as described herein, whose effect on the dispersion rate and/or average velocity of fluidic materials flowed through the channel is used to separate such fluidic materials without the use of, e.g., separation matrices, electrophoresis, etc.

The microfluidic devices of the invention typically include at least one main channel (herein, as termed a specifically configured microchannel and/or a "regular" microchannel), where, e.g., analysis, separations, etc. are performed, but may include two or more main channels in order to multiplex the number of analyses being carried out in the microfluidic device at any given time. Typically, a single device will include from about 1 to about 100 or more separate main channels, which main channel(s) are often ones specifically configured in cross-sectional areas and/or "regular" cross-sectional channels for separation as well. In most cases, the main channel is intersected by at least one other microscale channel disposed within the body of the device. Typically, the one or more additional channels are used, e.g., to bring the samples, test compounds, assay reagents, etc. into the main channel, in order to carry out the desired assay, separation, etc. Additionally, the main channel can be intersected by one or more shunt microchannels as well.

The reservoirs or wells of microfluidic devices incorporating the methods and devices of the current invention are locations at which samples, components, reagents, and the like are added into the device for assays, etc. to take place. Introduction of these elements into the system is carried out as described herein. The reservoirs are typically placed so that the sample or reagent is added into the system upstream from the location at which it is used. For example, a dilution buffer is added upstream from the source of a reagent if the sample is to be diluted before reaction with the reagent. Alternatively, waste wells or reservoirs are used to store samples after a reaction or assay has been completed. The removal of the completed samples provides space in the channels to load and incubate other samples. In this fashion, the devices of the invention are optionally used in a high throughput manner. The throughput is maintained by continuously loading, incubating, and unloading samples into and from the incubation channels of the device.

In the present invention, a dilution buffer is typically added into a main channel upstream of a shunt channel, so that the increase in flow rate due to the addition of buffer material downstream of its entry point may be counteracted by the reduction in pressure due to the shunt channel. Reagent materials, on the other hand, are typically added downstream of a shunt channel so that they are added after the downstream flow rate in the main channel has been reduced, so that smaller quantities of reagent are added.

In these systems, a "capillary element" (a channel in which fluidic materials can be moved from a source to a microscale element) or other similar pipettor element is temporarily or permanently coupled to a source of fluidic material. The source of the fluidic material can be internal or external to the microfluidic device comprising the capillary element. Example sources include microwell plates, membranes, or other solid substrates comprising lyophilized components, wells, or reservoirs in the body of the microscale device itself, etc.

For example, the source of a cell type, sample, or buffer can be a microwell plate external to the body structure of the microfluidic device, having at least one well with a sample of interest, i.e., the sample plug(s) and/or buffer plug(s) to be drawn into the device will be within the microwell plate. Alternatively, the fluidic material source is a well or reservoir disposed on the surface or within the body of the structure of the microfluidic device comprising a selected cell type, component, reagent, etc.; a container external to the body structure of the microfluidic device comprising at least one compartment comprising the selected particle type, component, reagent, etc.; or a solid phase structure comprising the selected cell type, reagent, etc. in lyophilized or otherwise dried form.

Manipulation/Control of Fluidic Material within Microfluidic Devices

The present invention provides methods and devices for manipulating and controlling aliquots of fluidic materials in microfluidic devices and systems by utilizing (and/or changing) differences in dispersion rate and/or average velocity of different fluidic materials as such materials pass through the channels of the device or system. The present invention is applicable to both homogeneous and non-homogeneous assays.

As used herein, the term "dispersion" refers to the convection-induced, longitudinal dispersion of material within a fluid medium due to velocity variations across streamlines, e.g., in pressure driven flow systems, electrokinetically driven flow systems around curves and corners, and electrokinetically driven flow systems having non-uniform buffer ionic concentrations, e.g., plugs of high and low salt solutions within the same channel system. For the purposes of the present invention, dispersion is generally defined as that due to the coupling between flow and molecular diffusion, i.e., Taylor dispersion. In this regime, the time-scale for dispersion due to convective transport is long or comparable to the time scale for molecular diffusion in the direction orthogonal to the flow direction. For discussions on dispersion and Taylor dispersion in particular, see, e.g., Taylor et al., *Proc. Roy. Soc. London*, (1953) 219A:186-203; Aris, *Proc. Roy. Soc. London* (1956) A235:67-77; Chatwin et al., *J. Fluid Mech.* (1982) 120:347-358; Doshi et al., *Chem. Eng. Sci.* (1978) 33:795-804; and Guell et al., *Chem. Eng. Comm.* (1987) 58:231-244, each of which is incorporated herein by reference for all purposes. Channel design optimization in light of dispersion and diffusion of serially introduced reagents is described in "Methods and Software for Designing Microfluidic Devices," U.S. Ser. No. 09/277,367 filed Mar. 26, 1999, by Chow et al.

and in "Optimized High-Throughput Analytical System," U.S. Ser. No. 09/233,700 filed Jan. 19, 1999, by Kopf-Sill et al., which are incorporated herein by reference for all purposes. For more information on dispersion as it relates to high throughput in microfluidic devices, see, e.g., U.S. Pat. No. 6,150,119 issued Nov. 21, 2000, entitled "Optimized High-Throughput Analytical System" to A. Kopf-Sill et al., which is incorporated herein by reference for all purposes.

In typical microfluidic devices fluid is moved through micro-etched channels via electrokinetic flow (electrophoresis or electroosmosis) or through the application of small pressure differentials. In the absence of bends in the channels, electrokinetically driven flows do not produce convective dispersion. In electrokinetic flow, all solute molecules across the microchannel travel with the same velocity, hence no shear results from this motion, and therefore no Taylor dispersivity is produced. However, pressure driven flows of small molecule fluidic material i.e., colloidal material (less than 1 μm), which may include small molecular weight material, through a channel (e.g., a microchannel as is used herein) can lead to large amounts of dispersion. This is also true when a pressure gradient is produced unintentionally, e.g., through the result of hydrostatic pressure differentials or mismatches in electrokinetic flow rates along a microchannel. The cause of such dispersion is that the convective velocity of the fluidic material is lower near the walls than it is in the center of the microchannel, and thus a plug of fluidic material that starts out as discrete will spread out as convection proceeds in the axial direction. Ultimately this convection spreading process is cut off by diffusion across streamlines. This results in an effective dispersivity "K." For example, in flow of a fluidic material through a tube, the dispersivity in the axial direction is given by $$\frac{K}{D} = 1 + \frac{1}{48}\left(\frac{Ua}{D}\right)^2$$

where U is the average velocity in the tube, a is the tube radius, and D is the molecular diffusivity. See, Taylor, *Proc. Roy. Soc.* (1953) 219A:186-203.

In a rectangular or isotropically etched channel that is substantially rectangular, the dispersivity is determined by $$\frac{K}{D} = 1 + \frac{1}{210}f\left(\frac{d}{w}\right)\left(\frac{Ud}{D}\right)^2$$

where d is the channel depth and w is the channel width. The function $f(d/w)$ is dependent on the aspect ratio of the channel. For very small (d/w) ratio, $f$ approaches the value 8 in a rectangular channel. See Doshi et al., Chem. Eng. Sci (1978) 3:795-804.

In the microchannels of the present invention, the dispersion of small molecule fluidic material is dictated by the Taylor-Aris dispersion mechanism, which is an interplay between convection and molecular diffusion. For the majority of systems involving small molecule fluidic materials, the Taylor dispersivity (or Taylor-Aris dispersion) is much greater than the molecular diffusivity, and thus the Taylor dispersivity predominantly controls the spread of the plug or band (i.e., the aliquot) of the fluidic material. The Taylor-Aris dispersion of a fluidic material can be modified by modifying the cross-sectional geometry of the conduit (e.g., microchannel) in which the material flows.

Figure 7:
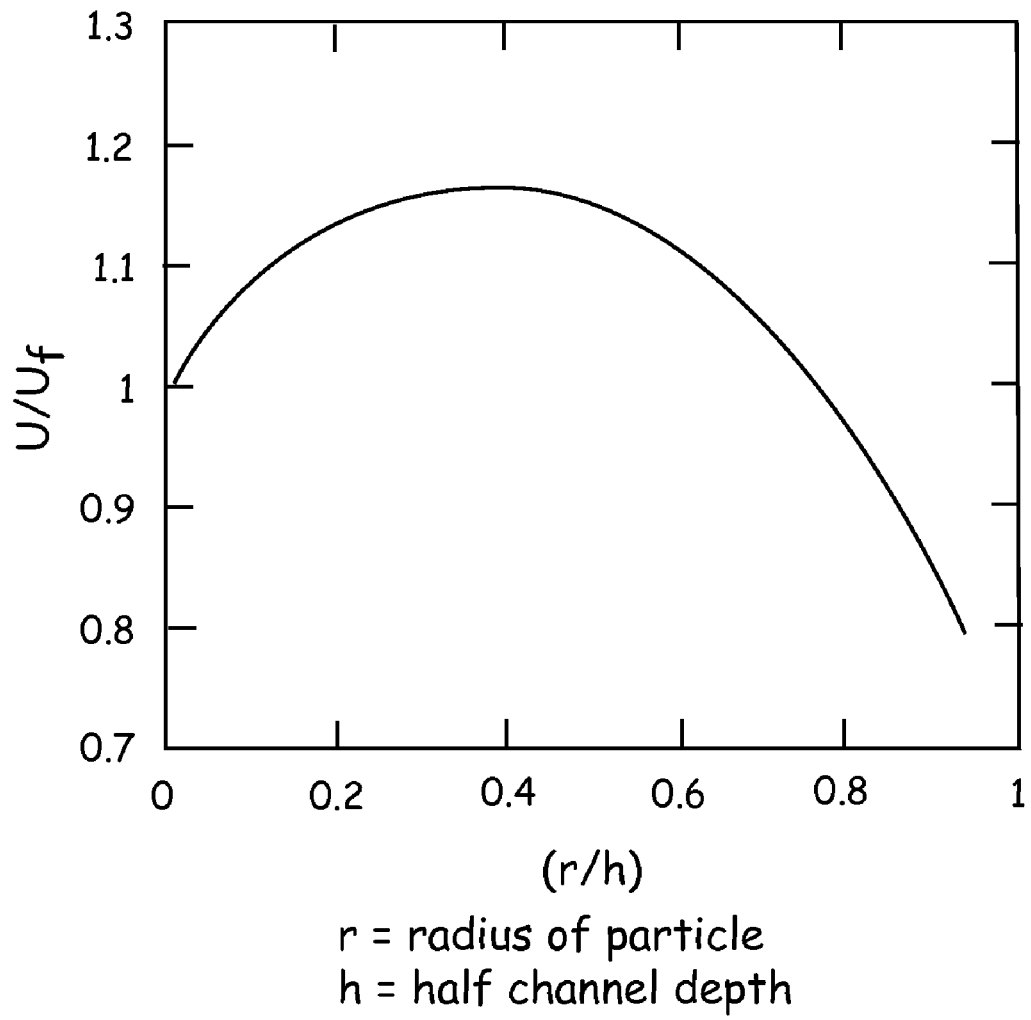
FIG. 7 illustrates average particle velocity relative to the average fluid velocity versus normalized particle size in a two-dimensional channel with Poiseuille flow.

The dispersion of fluidic materials that are not small, e.g., cells, beads, etc., is not controlled by Taylor-Aris dispersion. Instead, because of their large size, thermal diffusion is negligible and their dispersion is controlled by convection only. Consequently, the dispersion rate of non-Brownian materials, e.g., cells, beads, etc., is generally larger than that for colloidal or Brownian fluidic materials in, e.g., microchannels. Additionally, they can flow at an average velocity different than that of the small molecule or Brownian fluidic materials. The difference in velocity is determined by two factors. First, the center of mass of larger non-Brownian fluidic materials (i.e., non-small molecules) is excluded from the region near the channel wall (i.e., the slower flowing region) comparable to the radius of the non-small molecule materials. This factor causes the non-small molecular non-Brownian materials to flow faster than the small molecule materials in the same channel. Second, hydrodynamic interactions with the wall slow down the flow of the non-Brownian materials compared to the Brownian or small molecular materials in the same streamline. The importance of these two opposing factors can be controlled by varying the ratio of the half channel depth (h) to the radius of the non-Brownian materials (r) to the half channel depth (h). At very small values of (r/h), the velocity ratio of the non small to small molecule fluidic materials reaches unity. As the ratio (r/h) increases, the velocity ratio increases initially and then decreases as is shown by Staben et al. in "Motion of a particle between two parallel plane walls in low-Reynolds number Poiseuille Flow" Physics of Fluid. Staben et al. show that particles that have diameters that are 42% of the channel depth have a maximum average velocity that is greater than the average fluid velocity; however, this is not the case for particles that have diameters greater than 82% of the channel depth. These large particles were found to have smaller average velocities than the fluid. See FIG. 7 illustrating the average particle velocity relative to the average fluid velocity in relation to particle size in a two-dimensional channel with Poiseuille flow. While the differences in dispersion rates and/or average velocity between small molecule fluidic materials and non-small molecule fluidic materials such as cells, as outlined above, can be problematic in some assay situations, the current invention utilizes such in the methods and devices herein to produce desired manipulations/controls of the fluidic materials.

The current invention cleverly takes advantage of the varying dispersion rates and/or average velocity of small molecule fluidic materials (which are governed by Taylor-Aris dispersion) and non-small molecule fluidic materials, such as cells (which are governed solely by convection). For example, the methods and devices of the current invention utilize the above disparities to perform separations between fluidic materials without having to resort to use of, e.g., electrophoresis, gel matrices, etc. Furthermore, again, as illustrated in more detail below, the methods and devices of the current invention utilize the differences in dispersion rates and/or average velocity produced by changed cross-sectional geometries of microchannels to manipulate/control aliquots of fluidic material (e.g., to keep disparate fluidic materials such as cells and small molecule compounds together in the same fluidic plug or, conversely, to separate such fluidic materials into different fluidic plugs).

Figure 2C:
Figure 2D:
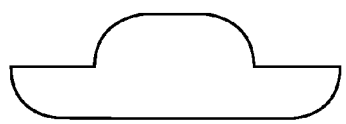
Figure 2E:

For example, a microfluidic device can be designed to include at least one microchannel that includes at least one region comprising a first cross-sectional geometry along its length which is shaped and dimensioned to enhance a dispersion of at least one of at least two differently sized particles flowing in a fluid through the microchannel such that the at least two particles have substantially the same average velocity in the at least one region of the microchannel, as shown for example in FIGS. 2C, 2D, and 2E, wherein the microchannel includes lateral wings that are shallower than a central portion of the channel. Such a configuration with shallower side wings can help enhance the dispersion of small compounds such as test compounds, and thus further increase their average velocity, relative to flowing cells in the microchannel in order to substantially match the average velocity of the compounds relative to the average velocity of the cells in the microchannel. Such a cross-sectional geometry configuration may find particular applicability in high-throughput screening applications as described, for example, in U.S. Pat. No. 5,942,443, which is incorporated by reference herein in its entirety. In high-throughput screening of cell-based assays as described in the '443 patent, the compounds (e.g., potential drug candidates) are brought in as discrete bands in a serial manner, and the throughput is dictated by how far apart the compound bands must be spaced. In cell-based assays, cells typically move at an average velocity and dispersion rate that is higher than those of the compounds. To avoid dispersion between the compound bands, typically the bands are increased in size to ensure that some of the cells are always in contact with a given compound for a required incubation period. However, the throughput of the system decreases with long compound bands. In order to substantially match the velocity and/or dispersion of the cells and compounds (or any other differently sized/charged/mass species) in the microchannel, the cross-sectional geometry of the microchannel can be configured as described above with reference to FIGS. 2A and 2C-E to enhance the dispersion of the small compounds relative to the cells so that the average velocity of the two species is substantially equal.

Figure 2F:
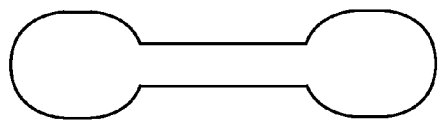
Figure 2G:
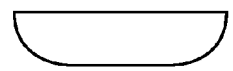
Figure 2H:
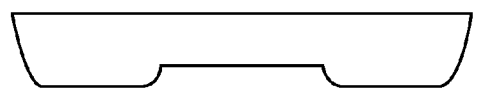

On the other hand, in other applications such as cell-washing, one may want to enhance the differential velocities of particles or molecules (e.g., target drug compounds versus cells) flowing down the microchannel. Again, the cross-sectional geometry of the microchannel can be manipulated to accomplish that goal. For example, a microfluidic device can be designed to include at least one microchannel that has at least one (or more) region along its length having a first cross-sectional geometry that is shaped and dimensioned to enhance a differential velocity of at least one of at least two differently sized particles flowing in a fluid through the microchannel, such as shown in FIGS. 2F and 2H, for example. Of course, the microchannel can further include at least a second region having a second cross-sectional geometry that is dimensioned and shaped to alter the dispersion of at least one of the least two differently sized particles flowing through the microchannel such that the particles have a different average velocity as they flow through the microchannel, as discussed above.

As used herein, the term "cross-sectional geometry," "channel geometry," "geometry," etc. is to be understood to optionally include the dimension/size of the channel (i.e., of the elements of the channel such as height, depth, wall curvature, etc.) as well as the layout/pattern of the channel (i.e., the arrangement of the elements of the channel such as wall height, curvature, placement of any troughs/ridges/etc.). In other words, either or both of the dimension/size of a microchannel (or its elements) or the layout/pattern of a microchannel (i.e., of its elements) are included within its "cross-sectional geometry" and are manipulated herein in order to perform the separations, etc. of the current invention.

As used herein, some microchannels are described as "regular," "non-specifically configured," "rectangular," "substantially rectangular," or the like (e.g., the separation of mixed fluidic materials in "regular" microchannels without the use of electrophoresis or matrices, etc.). Such channels are typically ones similar to that illustrated in cross-section in FIG. 1. As shown in FIG. 1, the microchannel has basically vertical sides and a horizontal bottom with rounded transitions between the side walls and the bottom (i.e., depth d, width l, side transition regions of radius r as used in FIG. 1). Such microchannels are typically fabricated by isotropic etching processes as used to construct the microfluidic devices of the current invention. It is to be understood that other similarly shaped microchannels (i.e., ones of slightly different character but basically the same shape) are also included in the preceding terms (e.g., "regular," etc.). For example, the bottom of a regular microchannel can comprise a concave or "half-moon" shape, etc. The area of a regular microchannel (e.g., one as is shown in FIG. 1) is given by the equation:

$$A = r^2 \left( \frac{\pi}{2} + \frac{l}{d} \right)$$

Additionally, as used herein, some microchannels are described as "configured," "specifically configured," etc. Such channels can comprise a myriad of channel shapes depending upon the specific end result desired. For example, non-limiting exemplars of specifically configured microchannels are shown in FIGS. 2A, 2C-2F, and 2H. Such microchannels are similar in some ways to a "regular" microchannel as shown in FIG. 1, but contain further complexity in their cross-sectional geometry. While the regular microchannel in FIG. 1 can be produced by typical isotropic-etching techniques, the more complex "specifically configured" microchannels in FIG. 2 are optionally fabricated through, e.g., a double (or triple, etc.) etching technique. Additionally, and/or alternatively, two substrate layers can be etched (either isotropically or otherwise) and then placed (e.g., joined, bonded, etc.) together to form the microchannel. Each substrate layer can be etched in either the same or different geometry, thus resulting in either a symmetrical channel geometry (see, e.g., FIG. 2E) or an asymmetrical channel geometry (see, e.g., FIG. 2D). Again, depending upon the specific end result desired (e.g., minimizing Taylor-Aris dispersion; separating, either quickly or slowly, a plug comprising a number of mixed fluidic materials into separate bands of single fluidic material; keeping disparate types of fluidic materials, such as, e.g., cells and small molecule compounds, together in the same plug; etc.), the cross-sectional geometry of specifically configured microchannels varies in different embodiments of the current invention, and FIG. 2 represents only several of the many possible configurations of the invention.

The cross-sectional geometry of microchannels of the present invention, be they regular or specifically configured, can change over their length. In other words, a microchannel can change from, e.g., a channel as shown in FIG. 1 to, e.g., one having a perpendicular transition between the side walls and the bottom, or, e.g., from one as shown in FIG. 1 to any one as shown in FIG. 2 (or any other specifically configured microchannel) all depending upon the particular needs of the assays/systems used.

In order to correctly manipulate/control the dispersion rates and/or average velocity of the fluidic materials flowed through the "regular" channels involved in the methods and devices of the current invention, the dispersivity of materials flowing in the microchannels used in the microfluidic devices of the current invention is determined. This is done by using the method of moments (see, e.g., Aris, *Proc. Roy. Soc.* (1956)

235A:67-77) to calculate the dispersivity for a channel of particular cross-section geometry. Such process involves first calculating the velocity field within the channel, wherein u is the unidirectional velocity in the direction z. The dimensionless velocity distribution is controlled by the Poisson equation:

$$\nabla^{*2} u^* = -1; \; u^*|_{\partial D^*} = 0$$

wherein the unidirection velocity is rendered dimensionless with respect to the characteristic velocity $U_c$, and all lengths are held dimensionless with respect to the channel depth d. Thus, $$u^* = \frac{u}{U_c};$$

$$U_c = \frac{\left(-\frac{\Delta p}{L}\right) d^2}{\mu}.$$

Because there is no variability in the direction z, the Laplacian $\nabla^{*2}$ is the two-dimensional Laplacian. Once the dimensionless velocity $u^*$ is determined, the average velocity in channel U is determined by:

$$U = U_c \frac{1}{A^*} \int_{D^*} u^* dA^*$$

wherein $A^* = A/d^2$. Once the above velocity is determined, it is used to re-normalize velocity $u^*$ by:

$$\hat{u} = \frac{u}{U}.$$

The determination for Taylor-Aris dispersivity thus reduces to the simple integral:

$$\frac{K}{D} = 1 + \left(\frac{Ud}{D}\right)^2 \frac{1}{A^*} \int_{D^*} \hat{u} \hat{g} \, dA^*$$

wherein the function $\hat{g}$ is the solution to the following problem:

$$\nabla^{*2} \hat{g} = 1 - \hat{u};$$

$$\vec{\nabla} * \hat{g} \cdot \vec{n}\,|_{\partial D^*} = 0;$$

$$\int_{D^*} \hat{g} \, dA^* = 0.$$

While the above equations are used to determine dispersivity in channels of regular cross-sectional geometry (e.g., ones such as shown in FIG. 1 used to, e.g., separate mixed fluidic materials without the use of electrophoresis, matrices or the like), by accounting for the correct cross-sectional geometry, the equations can be adapted for use with microchannels of specifically configured cross-sectional geometry (e.g., ones used to keep specific fluidic materials, e.g., in the same fluidic plug or to separate such into separate plugs).

Illustrative Examples of Sample Microfluidic Device Incorporating Manipulation/Control of Aliquots of Fluidic Materials As stated previously, the use of pressure driven flow in microfluidic devices often leads to large amounts of Taylor dispersion. Furthermore, even use of electroosmotic flow or hydrostatic pressure driven flow can lead to occurrence of Taylor dispersion due to small pressure gradients that may arise due to mismatch of forces. The present invention utilizes the dependence of Taylor-Aris dispersivity on a microchannel's cross-sectional geometry to control (e.g., minimize) dispersion of materials in "specifically configured" microfluidic channels. The present invention also cleverly takes advantage of such differences in dispersion and/or flow rate to manipulate and control aliquots of fluidic materials in microfluidic devices. The present invention uses the mismatch of dispersion rates and/or average velocity between different fluidic materials in herein termed "regular" channels to allow separation between such fluidic materials without having to use, e.g., electrophoresis, separation matrices (e.g., gel matrices), etc. Additionally, the present invention specifically configures the cross-sectional geometry of microchannels in order to take advantage of, and to change, differences in dispersion rate and/or average velocity between different fluidic materials in specifically configured microchannels (i.e., in microchannels whose cross-sectional geometry has been specifically configured to achieve such desired result).

Not only can configuration of microchannel cross-sectional geometry, as described herein, allow for the separation of different fluidic materials based upon varying dispersion rates and/or average velocity, but such configuration can also allow non-separation of different fluidic materials. In other words, the specifically configured microchannels herein can allow fluidic materials which would normally separate (i.e., in a "regular" channel shape) in flow due to their different dispersion/average velocity rates to NOT separate, and thus stay in the same "plug" or aliquot in a microchannel.

By having the specific configuration of a microchannel change over its course, myriad effects can be achieved. For example, one fluidic material can be "washed" by another fluidic material. In such a case, e.g., cells (containing a specific receptor) and a ligand specific for such receptor can be mixed into the same aliquot and flowed through a specifically configured microchannel of the present invention. The specific configuration of the microchannel thus keeps the, e.g., cells and ligand together in the same plug where otherwise the cells and the ligand would tend to separate into separate bands due to their different rates of dispersion and/or average velocity. Once the cells and ligand have been in each other's presence for the required period of time, the mixed plug can flow through a different section of microchannel which has been specifically configured to maximize the differences between the dispersion rates and/or average velocity of the two components and thus separate them into different bands. Alternatively, the mixed plug could be flowed through a "regular" cross-sectional geometry channel in order for the cells to be washed free of the unbound ligand, again, due to differences between the dispersion rates and/or average velocity of the two components.

Sample plugs (i.e., discrete aliquots of sample) within microfluidic elements of microfluidic devices, such as those using the devices/methods of the current invention, often undergo a blurring or smearing of their original boundaries. Such blurring is typically caused by diffusion and/or dispersion of the sample plug.

The methods and devices of the present invention are useful in numerous situations, for example, they can be used to maximize throughput of serially introduced samples by preventing or reducing unwanted intermingling of fluidic materials in microfluidic devices or systems (i.e., by reducing dispersion of fluidic plugs). The "throughput" of a microfluidic device/system/channel is typically defined as the number of different materials that can be serially introduced into the device/system/channel per unit time. Compounds that are screened at rates greater than one compound per minute within a single channel are generally termed high throughput, while screening of compounds at a rate greater than one compound per 10 seconds generally falls into the ultra-high throughput category. Decreasing the amount of unwanted intermingling of sample plugs allows for minimization of spacing between serially introduced materials, e.g., samples, thus allowing a greater number of different materials, e.g., samples, to be serially introduced into the microfluidic device per unit time. The closer that plugs are able to be loaded, the more plugs that can be analyzed per unit time.

Spacers and/or buffers are optionally used to keep samples separated and/or prevent mixing of samples. For example, a buffer is optionally loaded into a channel after each sample plug in order to separate samples from one another and prevent contamination between samples. A sample plug includes an initial sample aliquot and any products produced by incubation or reaction of the initial sample aliquot. The buffer plugs optionally can comprise immiscible fluids to decrease diffusion. Buffer plug lengths are calculated in the same way as sample plug lengths, e.g., based on diffusivity and/or dispersion of the material. For example a buffer plug is typically 500 µm to 5 mm, preferably 600 µm to 3 mm or 850 µm 1 mm. The last buffer plug loaded or added into a channel or the device is optionally longer, e.g., 500 um to about 10 mm, to, e.g., allow for flow pinching.

As stated previously, the elements (i.e., methods and devices) of the current invention can be incorporated into numerous microfluidic devices that perform any number of different assays, tasks, etc. Whenever throughput needs to be optimized, the elements of the current invention can be combined and interlaced to help achieve proper (or more efficient) throughput. High throughput assays are useful in, e.g., diagnostic assays, genomic assays, and, in particularly preferred aspects, pharmaceutical screening assays. The various types of assays that benefit from such systems and methods as are found within the present invention are described generally in Published International Patent Application Nos. 98/00231 and 98/00705, which are incorporated herein by reference in their entirety for all purposes.

Additionally, the methods and devices of the current invention are readily incorporated into numerous microfluidic devices that require manipulation/control of fluidic materials to, e.g., keep mixed fluidic materials in the same plug(s) and/or separate plugs of mixed fluidic materials into separate plugs (without having to resort to use of separating matrices and with or without use of electrophoresis). These systems are described in numerous publications by the inventors and their coworkers. These include certain issued U.S. patents, including U.S. Pat. Nos. 5,699,157 (J. Wallace Parce) issued Dec. 16, 1997, 5,779,868 (J. Wallace Parce et al.) issued Jul. 14, 1998, 5,800,690 (Calvin Y. H. Chow et al.) issued Sep. 1, 1998, 5,842,787 (Anne R. Kopf-Sill et al.) issued Dec. 1, 1998, 5,852,495 (J. Wallace Parce) issued Dec. 22, 1998, 5,869,004 (J. Wallace Parce et al.) issued Feb. 9, 1999, 5,876,675 (Colin B. Kennedy) issued Mar. 2, 1999, 5,880,071 (J. Wallace Parce et al.) issued Mar. 9, 1999, 5,882,465 (Richard J. McReynolds) issued Mar. 16, 1999, 5,885,470 (J. Wallace Parce et al.) issued Mar. 23, 1999, 5,942,443 (J. Wallace Parce et al.) issued Aug. 24, 1999, 5,948,227 (Robert S. Dubrow) issued Sep. 7, 1999, 5,955,028 (Calvin Y. H. Chow) issued Sep. 21, 1999, 5,957,579 (Anne R. Kopf-Sill et al.) issued Sep. 28, 1999, 5,958,203 (J. Wallace Parce et al.) issued Sep. 28, 1999, 5,958,694 (Theo T. Nikiforov) issued Sep. 28, 1999, 5,959,291 (Morten J. Jensen) issued Sep. 28, 1999, 5,964,995 (Theo T. Nikiforov et al.) issued Oct. 12, 1999, 5,965,001 (Calvin Y. H. Chow et al.) issued Oct. 12, 1999, 5,965,410 (Calvin Y. H. Chow et al.) issued Oct. 12, 1999, 5,972,187 (J. Wallace Parce et al.) issued Oct. 26, 1999, 5,976,336 (Robert S. Dubrow et al.) issued Nov. 2, 1999, 5,989,402 (Calvin Y. H. Chow et al.) issued Nov. 23, 1999, 6,001,231 (Anne R. Kopf-Sill) issued Dec. 14, 1999, 6,011,252 (Morten J. Jensen) issued Jan. 4, 2000, 6,012,902 (J. Wallace Parce) issued Jan. 11, 2000, 6,042,709 (J. Wallace Parce et al.) issued Mar. 28, 2000, 6,042,710 (Robert S. Dubrow) issued Mar. 28, 2000, 6,046,056 (J. Wallace Parce et al.) issued Apr. 4, 2000, 6,048,498 (Colin B. Kennedy) issued Apr. 11, 2000, 6,068,752 (Robert S. Dubrow et al.) issued May 30, 2000, 6,071,478 (Calvin Y. H. Chow) issued Jun. 6, 2000, 6,074,725 (Colin B. Kennedy) issued Jun. 13, 2000, 6,080,295 (J. Wallace Parce et al.) issued Jun. 27, 2000, 6,086,740 (Colin B. Kennedy) issued Jul. 11, 2000, 6,086,825 (Steven A. Sundberg et al.) issued Jul. 11, 2000, 6,090,251 (Steven A. Sundberg et al.) issued Jul. 18, 2000, 6,100,541 (Robert Nagle et al.) issued Aug. 8, 2000, 6,107,044 (Theo T. Nikiforov) issued Aug. 22, 2000, 6,123,798 (Khushroo Gandhi et al.) issued Sep. 26, 2000, 6,129,826 (Theo T. Nikiforov et al.) issued Oct. 10, 2000, 6,132,685 (Joseph E. Kersco et al.) issued Oct. 17, 2000, 6,148,508 (Jeffrey A. Wolk) issued Nov. 21, 2000, 6,149,787 (Andrea W. Chow et al.) issued Nov. 21, 2000, 6,149,870 (J. Wallace Parce et al.) issued Nov. 21, 2000, 6,150,119 (Anne R. Kopf-Sill et al.) issued Nov. 21, 2000, 6,150,180 (J. Wallace Parce et al.) issued Nov. 21, 2000, 6,153,073 (Robert S. Dubrow et al.) issued Nov. 28, 2000, 6,156,181 (J. Wallace Parce et al.) issued Dec. 5, 2000, 6,167,910 (Calvin Y. H. Chow) issued Jan. 2, 2001, 6,171,067 (J. Wallace Parce) issued Jan. 9, 2001, 6,171,850 (Robert Nagle et al.) issued Jan. 9, 2001, 6,172,353 (Morten J. Jensen) issued Jan. 9, 2001, 6,174,675 (Calvin Y. H. Chow et al.) issued Jan. 16, 2001, 6,182,733 (Richard J. McReynolds) issued Feb. 6, 2001, 6,186,660 (Anne R. Kopf-Sill et al.) issued Feb. 13, 2001, 6,221,226 (Anne R. Kopf-Sill) issued Apr. 24, 2001, 6,233,048 (J. Wallace Parce) issued May 15, 2001, 6,235,175 (Robert S. Dubrow et al.) issued May 22, 2001, 6,235,471 (Michael Knapp et al.) issued May 22, 2001, and 6,238,538 (J. Wallace Parce et al.) issued May 29, 2001.

These systems are also described in various PCT applications by the inventors including, e.g., WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, WO 99/44217, WO 99/56954, WO 99/64836, WO 99/64840, WO 99/64848, WO 99/67639, WO 00/07026, WO 00/09753, WO 00/10015, WO 00/21666, WO 00/22424, WO 00/26657, WO 00/42212, WO 00/43766, WO 00/45172, WO 00/46594, WO 00/50172, WO 00/50642, WO 00/58719, WO 00/60108, WO 00/70080, WO 00/70353, WO 00/72016, WO 00/73799, WO 00/78454, WO 01/02850, WO 01/14865, WO 01/17797, and WO 01/27253.

FIG. 3 illustrates one non-limiting example of a microfluidic device that incorporates methods and devices of the present invention. The microfluidic device as shown in FIG. 3 comprises body structure 302, in which are disposed various microchannels, reservoirs, etc. Specifically, channel 306 comprises a regular cross-sectional geometry (as described herein). Channel 304 comprises a channel of specifically configured cross-sectional geometry (as described herein), see, e.g., FIG. 2A-H for non-limiting examples of specifically configured microchannels. Both channel 304 and 306 are fluidly coupled to channel 324, which is optionally connected to capillary element 320, which accesses samples, etc. that are stored, e.g., outside of the device in, e.g., a microwell plate or the like. For example, capillary element 320 can access a microwell plate (or even numerous microwell plates provided in, e.g., a robotic armature) that contain a number of putative pharmaceutical compounds to be screened within the microfluidic device.

The fluidic material (or, more typically, the mixture of fluidic materials) in channel 324 is next mixed with, e.g., a buffer in order to, e.g., dilute the sample to a proper concentration for the necessary assays/reactions to occur and/or to help dilute unwanted sample storage materials such as DMSO. To accomplish such, in FIG. 3, a quantity of buffer is flowed into channel 324 from, e.g., buffer reservoir 310. Alternatively, additional fluidic materials in place of, or in addition to, buffers are optionally flowed into channel 324 from, e.g., reservoir(s) 308, 310, 312, or 314.

The fluidic material (or, again, more typically the mixture of fluidic materials) then is flowed from channel 324 into either (or both) channel 304 or 306. In channel 304 the fluidic materials are manipulated/controlled by having their dispersion rates and/or average velocity changed because of the specifically configured cross-sectional geometry of the microchannel (see, supra). The manipulation can entail, e.g., keeping the fluidic materials together in the same plug, separating mixed fluidic materials into separate plugs, etc. The fluidic materials in channel 304 are optionally flowed via any of the fluid transport mechanisms as described herein (e.g., electrokinetic flow, pressure driven flow, etc.). Although not displayed in FIG. 3, it will be appreciated that once mixed fluidic materials are separated into distinct plugs, such plugs can be analyzed, moved, considered, etc. separately of one another. Furthermore, it will also be appreciated that the cross-sectional geometry of channel 304 can change over the length of the channel, thereby producing different dispersion rates and/or average velocities at different locations along its length for the fluidic materials that are flowed through it.

Alternatively, or in addition, to the above, the fluidic materials in channel 324 can be flowed into channel 306 (i.e., the microchannel of regular cross-sectional geometry). As detailed above, channels of the invention such as 306, have a "regular" profile that is used to separate fluidic materials based upon their differing dispersion rates and/or average velocities within the channel without the use of other means of separation such as electrophoresis, separation matrices, etc.

A nice demonstration of separation of fluidic materials as occurs in channels such as 306 was demonstrated by the following experiment. Mixtures of various fluidic materials (as detailed below) were flowed through a microfluidic device comprising microchannels of regular cross-sectional geometry (as described herein) and the resulting separation of the various fluidic materials due to the differences in their dispersion rates and/or average velocity was detected via fluorescence.

Figure 5:
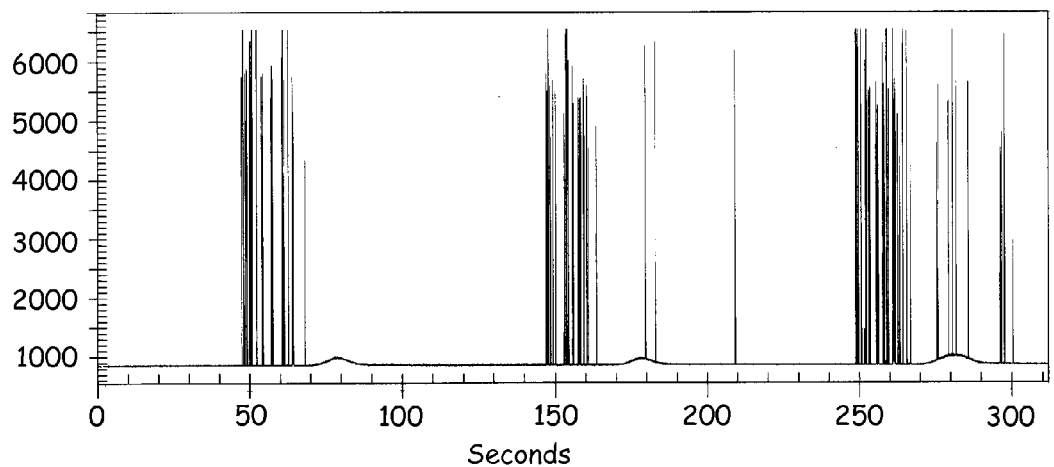
FIG. 5 is a graph representing separation of fluidic materials in a microchannel of regular cross-sectional geometry.

In one experiment, mixtures of fluorescein (at 0.5 micromolar) and 6 micrometer diameter latex beads in a cell buffer containing 0.1% BSA were aspirated into a 60-90 micrometer wide by 20 micrometer deep microchannel of regular cross-sectional geometry and flowed under negative 0.25 psi through the microfluidic device. The resulting separation is displayed in FIG. 5. The mixture was flowed in 10-second pulses into the channel. The transit time of the fluorescein was 55 seconds, while the transit time of the latex beads was 33 seconds. This conforms to the above described properties of flow of separation of molecules by flow through channels of regular cross-sectional geometry (see, above). In other words, the larger beads, since their flow was governed solely by convection, flowed through the channel faster than the small molecule fluorescein, which was subject to Taylor-Aris dispersion.

Figure 6A:
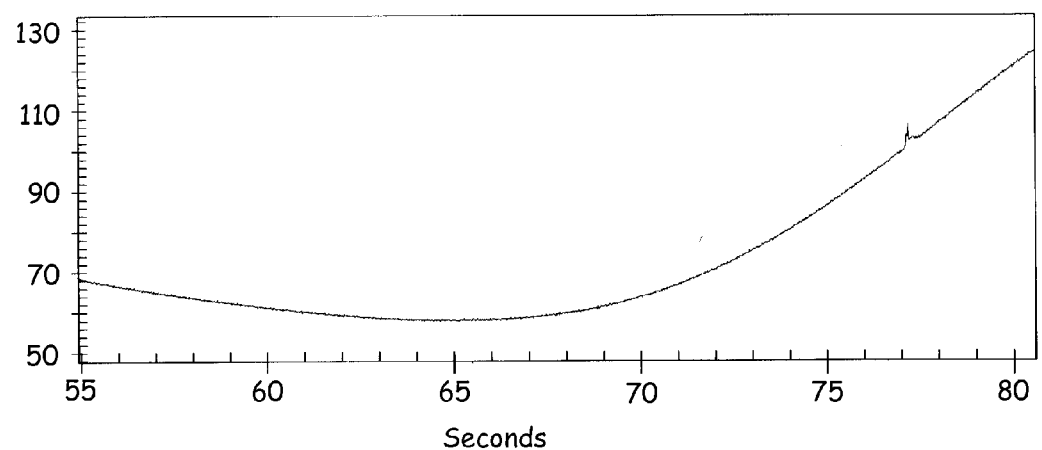
FIG. 6, panels A through E, are graphs representing separation of fluidic materials in a microchannel of regular cross-sectional geometry.

In another experiment demonstrating the methods and devices of the current invention, Jurkat cells were separated from fluorescein labeled monoclonal antibodies. See FIGS. 6A through 6E. In FIG. 6A, fluorescein labeled monoclonal antibodies at a 1/50 dilution of a 0.5 mg/ml solution, specific for MHC-II antigens (Ancell Corp., Bayport, Minn.), were flowed through a similar microchannel and in a similar fashion as for the above latex bead flow experiment.

Figure 6B:
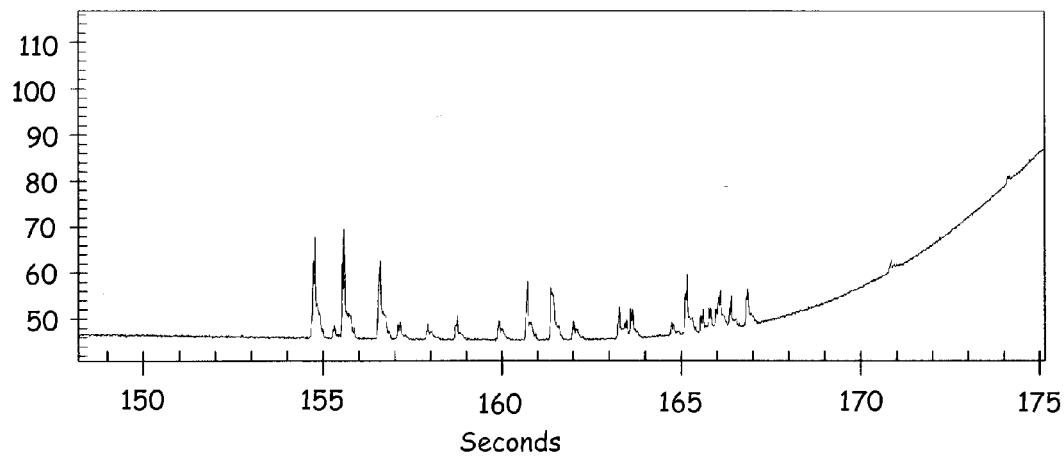
Figure 6C:
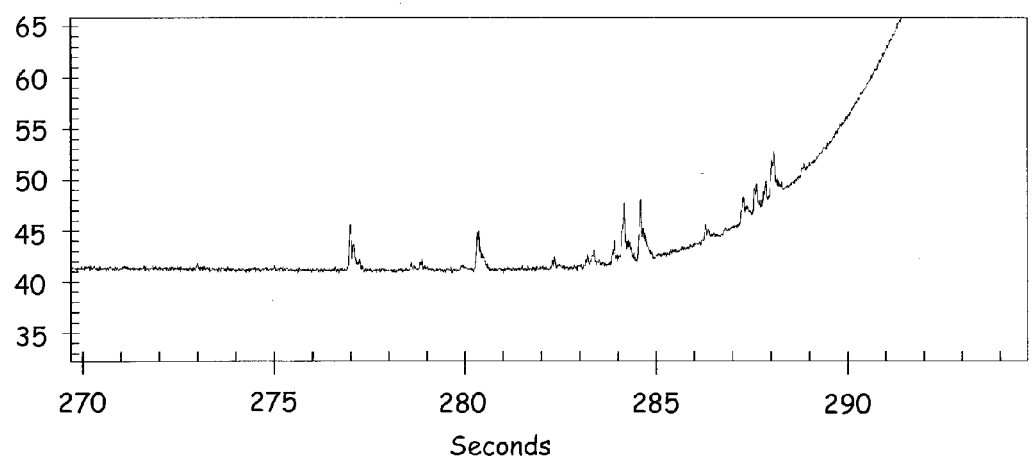

FIG. 6B shows separation of Jurkat cells associated with fluorescein labeled anti-MHC-II antibodies (Ancell Corp, Bayport, Minn.) at a 1/25 dilution of a 0.5 mg/ml solution, from unassociated fluorescein labeled anti-MHC-II antibodies, again, based upon their differing dispersion rates and/or average velocity. The Jurkat cells, which have approximately 200,000 MHC-II antigens on their cell surface, were present at a concentration of $5 \times 10^6$ per milliliter and the mixture was pulsed through the regular cross-sectional geometry microchannel in 10 second pulses. The graph of FIG. 6B shows the peaks of the Jurkat+labeled antibody flowing ahead of unbound labeled antibodies. A similar run is shown in FIG. 6c only utilizing a labeled antibody against CD3 antigen (Ancell, Corp., Bayport, Minn.) at a 1/25 dilution of a 0.5 mg/ml solution, on the Jurkat cells (Jurkat cells having approximately 30,000 CD3 antigens present on their cell surface). Again, the Jurkat+labeled antibodies flow ahead of the unbound labeled antibodies.

Figure 6D:
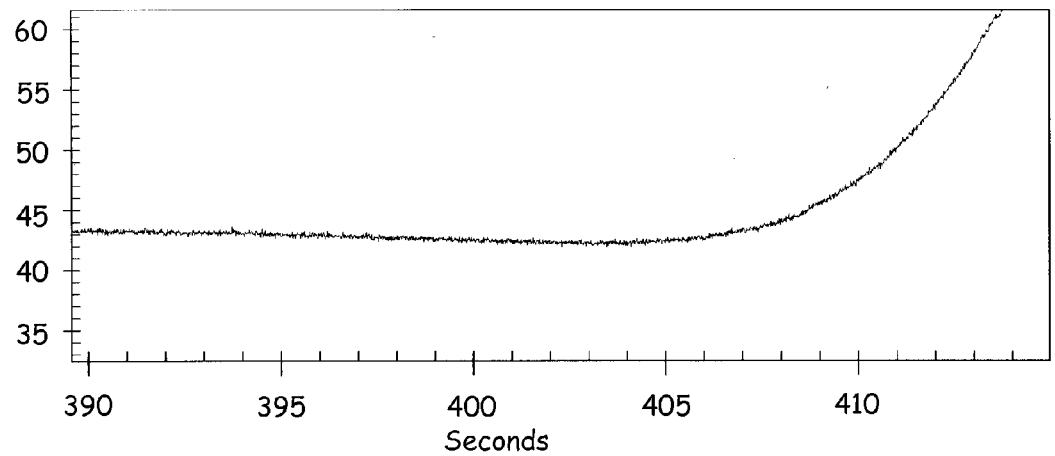

FIG. 6D illustrates a control experiment utilizing the same general parameters as those for the experiments displayed in FIGS. 6B and 6C, however, using anti-CD8 labeled antibodies (Ancell Corp.) at a 1/25 dilution of a 0.2 mg/ml solution. Because Jurkat cells do not display CD8 antigen, no cell+ antibody complexes were formed which would have separated due to their different dispersion/average velocity rate.

Figure 6E:
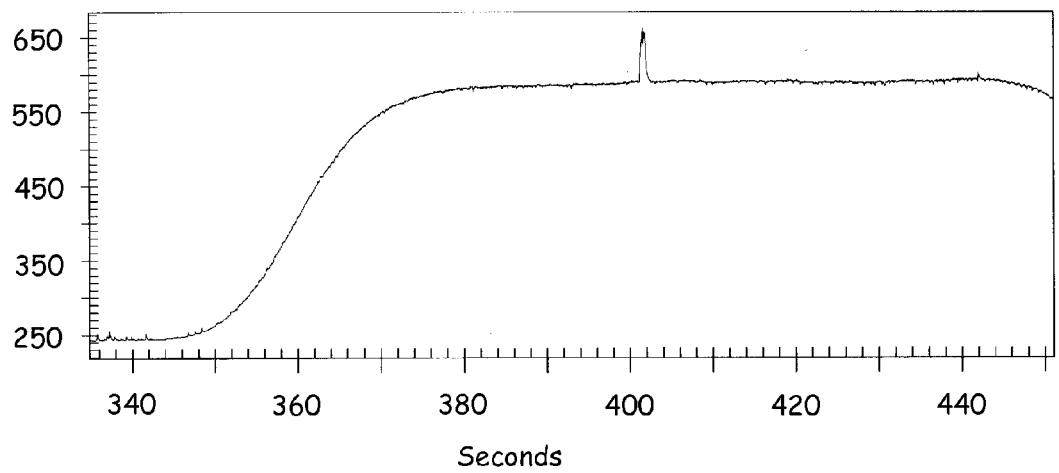

FIG. 6E illustrates another control experiment wherein, under similar conditions as for the experiment in FIG. 6C, Jurkat cells were flowed with labeled anti-CD3 antibodies. However, in this case, the pulses of mixed cells and antibodies (i.e., the amount of time such mixture was flowed into the microchannel) was 100 seconds instead of 10 seconds. Because there was no "space" (e.g., a buffer plug between the pulses), the separation of cells+antibodies from unlabeled antibodies due to their different dispersion/average velocity cannot be discerned.

The above examples, illustrate that the methods and devices of the current invention are easily adaptable to many different experimental situations and can be adapted to many different uses (e.g., separation of many different components of mixed samples, washing of compounds, minimization of sample plug dispersion, keeping components of different types (e.g., cells and labeled antibodies) together in the same fluidic plug, etc.).

Integrated Systems, Methods and Microfluidic Devices of the Invention

The microfluidic devices of the invention can include numerous optional variant embodiments including methods and devices for, e.g., fluid transport, temperature control, detection and the like.

As used herein, the term "microfluidic device" refers to a system or device having fluidic conduits or chambers that are generally fabricated at the micron to sub-micron scale, e.g., typically having at least one cross-sectional dimension in the range of from about 0.1 micrometer to about 500 micrometer. The microfluidic system of the current invention is fabricated from materials that are compatible with the conditions present in the specific experiments and/or separations to be performed on the specific samples, reagents, etc. under examination, etc. Such conditions include, but are not limited to, pH, temperature, ionic concentration, pressure, and application of electrical fields. The materials of the device are also chosen for their inertness to components of the experiments to be carried out in the device. Such materials include, but are not limited to, glass, quartz, silicon, and polymeric substrates, e.g., plastics, depending on the intended application.

Although the devices and systems specifically illustrated herein are generally described in terms of the performance of a few operations, or of one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein (e.g., upstream and/or downstream of separation of fluidic materials as described herein, etc.). Such upstream operations include such operations as sample handling and preparation, e.g., extraction, purification, amplification, cellular activation, labeling reactions, dilution, aliquotting, and the like. Similarly, downstream operations optionally include similar operations, including, e.g., further separation of sample components, labeling of components, assays and detection operations, electrokinetic or pressure-based injection of components or the like.

The microfluidic devices of the present invention can include other features of microscale systems, such as fluid transport systems that direct particle/fluid movement within and to the microfluidic devices as well as the flow of fluids to and through various channels or regions, etc. Various combinations of fluid flow mechanisms can be utilized in embodiments of the present invention. Additionally, various types of fluid flow mechanisms can be utilized in separate areas of microfluidic devices of the invention. For example, separation of fluidic materials can be carried out in non-manipulated microchannels (i.e., regular microchannels) using the methods of the invention and utilizing non-electrokinetic fluid flow. While in areas of the same microfluidic device which are not used for separation (or for other types of separation, e.g., in manipulated, or specifically configured, microchannels) of fluidic material using the methods of the invention can utilize electrokinetic fluid flow. Flow of fluidic components such as reagents, etc., can incorporate any movement mechanism set forth herein (e.g., fluid pressure sources for modulating fluid pressure in microchannels/micro-reservoirs/etc.; electrokinetic controllers for modulating voltage or current in microchannels/micro-reservoirs/etc.; gravity flow modulators; magnetic control elements for modulating a magnetic field within the microfluidic device; use of hydrostatic, capillary, or wicking forces; or combinations thereof).

The microfluidic devices of the invention can also include fluid manipulation elements such as parallel stream fluidic converters, i.e., converters that facilitate conversion of at least one serial stream of reagents into parallel streams of reagents for parallel delivery to a reaction site or reaction sites within the device. The systems herein optionally include mechanisms such as valve manifolds and a plurality of solenoid valves to control flow switching, e.g., between channels and/or to control pressure/vacuum levels in the, e.g., microchannels. Additionally, molecules, etc. are optionally loaded into one or more channels of a microfluidic device through one sipper capillary fluidly coupled to each of one or more channels and to a sample or particle source, such as a microwell plate.

In the present invention, materials such as cells, proteins, antibodies, enzymes, substrates, buffers, or the like are optionally monitored and/or detected, e.g., so that the presence of a component of interest can be detected, an activity of a compound can be determined, separation of fluidic materials can be monitored, or an effect of a modulator, e.g., on an enzyme's activity, can be measured. Depending upon the detected signal measurements, decisions are optionally made regarding subsequent fluidic operations, e.g., whether to assay a particular component in detail to determine, e.g., kinetic information or, e.g., whether, when, or to what extent to shunt a portion of a fluidic material from a main channel into a second channel (e.g., flowing a fluidic material into a second channel once it has been separated from a mixture of fluidic materials.

In brief, the systems described herein optionally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format. For example, the systems herein optionally include a valve manifold and a plurality of solenoid valves to control flow switching between channels and/or to control pressure/vacuum levels in the channels.

Temperature Control

Various embodiments of the present invention can control temperatures to influence numerous parameters or reaction conditions, e.g., those in thermocycling reactions (e.g., PCR, LCR). Additionally, the present invention can control temperatures in order to manipulate reagent properties, etc. In general, and in optional embodiments of the invention, various heating methods can be used to provide a controlled temperature in the involved miniaturized fluidic systems. Such heating methods include both joule and non-joule heating.

Non-joule heating methods can be internal, i.e., integrated into the structure of the microfluidic device, or external, i.e., separate from the microfluidic device. Non-joule heat sources can include, e.g., photon beams, fluid jets, liquid jets, lasers, electromagnetic fields, gas jets, electron beams, thermoelectric heaters, water baths, furnaces, resistive thin films, resistive heating coils, peltier heaters, or other materials, which provide heat to the fluidic system in a conductive manner. Such conductive heating elements transfer thermal energy from, e.g., a resistive element in the heating element to the microfluidic system by way of conduction. Thermal energy provided to the microfluidic system overall, increases the temperature of the microfluidic system to a desired temperature. Accordingly, the fluid temperature and the temperature of the molecules within, e.g., the microchannels of the system, are also increased in temperature. An internal controller in the heating element or within the microfluidic device optionally can be used to regulate the temperature involved.

These examples are not limiting and numerous other energy sources can be utilized to raise the fluid temperature in the microfluidic device.

Non-joule heating units can attach directly to an external portion of a chip of the microfluidic device. Alternatively, non-joule heating units can be integrated into the structure of the microfluidic device. In either case, the non-joule heating is optionally applied to only selected portions of chips in microfluidic devices (e.g., such as reaction areas, detection areas, etc.) or optionally heats the entire chip of the microfluidic device and provides a uniform temperature distribution throughout the chip A variety of methods can be used to lower fluid temperature in the microfluidic system, through use of energy sinks. Such an energy sink can be a thermal sink or a chemical sink and can be flood, time-varying, spatially varying, or continuous. A thermal sink can include, among others, a fluid jet, a liquid jet, a gas jet, a cryogenic fluid, a super-cooled liquid, a thermoelectric cooling means, e.g., peltier device or an electromagnetic field.

In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance: where POWER=power dissipated in fluid; I=electric current passing through fluid; and R=electric resistance of fluid.

$$POWER = I^2 R$$

The above equation provides a relationship between power dissipated ("POWER") to current ("I") and resistance ("R"). In some of the embodiments of the invention, wherein electric current is directed toward moving a fluid (where such is utilized, e.g., in areas of specially configured microchannel cross-sectional geometry where the dispersion rate and/or average velocity of fluidic materials are manipulated), a portion of the power goes into kinetic energy of moving the fluid through the channel. Joule heating uses a selected portion of the power to heat the fluid in the channel or a selected channel region(s) of the microfluidic device and can utilize in-channel electrodes. See, e.g., U.S. Pat. No. 5,965,410, which is incorporated herein by reference in its entirety for all purposes. Such a channel region is often narrower or smaller in cross section than other channel regions in the channel structure. The small cross section provides higher resistance in the fluid, which increases the temperature of the fluid as electric current passes therethrough. Alternatively, the electric current can be increased along the length of the channel by increased voltage, which also increases the amount of power dissipated into the fluid to correspondingly increase fluid temperature.

Joule heating permits the precise regional control of temperature and/or heating within separate microfluidic elements of the device of the invention, e.g., within one or several separate channels, without heating other regions where such heating is, e.g., unnecessary or undesirable. Because the microfluidic elements involved are extremely small in comparison to the mass of the entire microfluidic device in which they are fabricated, such heat remains substantially localized, e.g., it dissipates into and from the device before it affects other fluidic elements. In other words, the relatively massive device functions as a heat sink for the separate fluidic elements contained therein.

To selectively control the temperature of fluid or material of a region of, e.g., a microchannel, the joule heating power supply of the invention can apply voltage and/or current in several optional ways. For instance, the power supply optionally applies direct current (i.e., DC), which passes through one region of a microchannel and into another region of the same microchannel which is smaller in cross section in order to heat fluid and material in the second region. This direct current can be selectively adjusted in magnitude to complement any voltage or electric field applied between the regions to move materials in and out of the respective regions. In order to heat the material within a region, without adversely affecting the movement of a material, alternating current (i.e., AC) can be selectively applied by a power supply. The AC used to heat the fluid can be selectively adjusted to complement any voltage or electric field applied between regions in order to move fluid into and out of various regions of the device. Alternating current, voltage, and/or frequency can be adjusted, for example, to heat a fluid without substantially moving the fluid. Alternatively, the power supply can apply a pulse or impulse of current and/or voltage, which will pass through one microchannel region and into another microchannel region to heat the fluid in the region at a given instance in time. This pulse can be selectively adjusted to complement any voltage or electric field applied between the regions in order to move materials, e.g., fluids or other materials, into and out of the various regions. Pulse width, shape, and/or intensity can be adjusted, for example, to heat a fluid substantially without moving the fluid or any materials within the fluid, or to heat the material(s) while moving the fluid or materials. Still further, the power supply optionally applies any combination of DC, AC, and pulse, depending upon the application. The microchannel(s) itself optionally has a desired cross section (e.g., diameter, width or depth) that enhances the heating effects of the current passed through it and the thermal transfer of energy from the current to the fluid (e.g., in addition to, or alternative to, any cross-sectional geometry used to manipulate dispersion rate and/or average velocity of fluidic materials).

Because electrical energy is optionally used to control temperature directly within the fluids contained in the microfluidic devices, the methods and devices of the invention are optionally utilized in microfluidic systems which employ electrokinetic material transport systems, as noted herein. Specifically, the same electrical controllers, power supplies and electrodes can be readily used to control temperature contemporaneously with their control of material transport. See, infra. In some embodiments of the invention, the device provides multiple temperature zones by use of zone heating. On such example apparatus is described in Kopp, M. et al. (1998) "Chemical amplification: continuous-flow PCR on a chip" *Science* 280(5366):1046-1048.

As can be seen from the above, the elements of the current invention can be configured in many different arrangements depending upon the specific needs of the molecules, etc. under consideration and the parameters of the specific assays/reactions involved. Again, the above non-limiting illustrations are only examples of the many different configurations/embodiments of the invention.

Fluid Flow

A variety of controlling instrumentation and methodologies are optionally utilized in conjunction with the microfluidic devices described herein, for controlling the transport and direction of fluidic materials and/or materials within the devices of the present invention by, e.g., pressure-based or electrokinetic control, etc.

In the present system, the fluid direction system controls the transport, flow and/or movement of samples, other reagents, etc. into and through the microfluidic device. For example, the fluid direction system optionally directs the movement of one or more fluid (e.g., samples, buffers) etc. into, e.g., a microchannel where such fluidic materials are to be separated or a microchannel where diverse fluidic materials are to be kept together in a "plug." The fluid direction system also optionally directs the simultaneous or sequential movement of fluidic materials into one or more channels, etc. Additionally, the fluid direction system can optionally direct the shunting of portions of fluidic materials into shunt microchannels and the like.

The fluid direction system also optionally iteratively repeats the fluid direction movements to create high throughput screening, e.g., of thousands of samples. Alternatively, the fluid direction system optionally repeats the fluid direction movements to a lesser degree of iterations to create a lower throughput screening (applied, e.g., when the specific analysis under observation requires, e.g., a long incubation time when a higher throughput format would be counter productive) or the fluid direction system utilizes a format of high throughput and low throughput screening depending on the specific requirements of the assay. Additionally, the devices of the invention optionally use a multiplex format to help achieve high throughput screening, e.g., through use of a series of multiplexed sipper devices or multiplexed system of channels coupled to a single controller for screening in order to increase the amount of samples analyzed in a given period of time. Again, the fluid direction system of the invention optionally controls the flow (timing, rate, etc.) of samples, reagents, buffers, etc. involved in the various optional multiplex embodiments of the invention.

One method of achieving transport or movement of particles through microfluidic devices is by electrokinetic material transport. In general, electrokinetic material transport and direction systems include those systems that rely upon the electrophoretic mobility of charged species within an electric field applied to the structure. Such systems are more particularly referred to as electrophoretic material transport systems. In the current invention, electrokinetic transport is optionally used as the method of fluid transport when fluidic materials are manipulated (e.g., various fluidic materials kept together in a plug, or various materials separated from a single mixture into distinct plugs) in a microchannel whose cross-sectional geometry is specifically designed/configured to achieve the desired manipulation (e.g., a channel's shape is specifically configured to keep various fluidic materials together in a plug). However, electrokinetic transport is not a preferred fluid transport method when separation of fluidic materials is to be done in a non-configured microchannel (i.e., a "regular" cross-sectional shaped microchannel). In such cases, the preferred fluid transport method comprises, e.g., pressure based flow, wicking based flow, hydrostatic based flow, etc. See, below.

Electrokinetic material transport systems, as used herein, and as optional aspects of the present invention, include systems that transport and direct materials within a structure containing, e.g., microchannels, microreservoirs, etc., through the application of electrical fields to the materials, thereby causing material movement through and among the areas of the microfluidic devices, e.g., cations will move toward a negative electrode, while anions will move toward a positive electrode. Movement of fluids toward or away from a cathode or anode can cause movement of particles suspended within the fluid (or even particles over which the fluid flows). Similarly, the particles can be charged, in which case they will move toward an oppositely charged electrode (indeed, it is possible to achieve fluid flow in one direction while achieving particle flow in the opposite direction). In some embodiments of the present invention, the fluid and/or particles, etc. within the fluid, can be immobile or flowing.

For optional electrophoretic applications of the present invention, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel. A variety of electrokinetic controllers are described, e.g., in Ramsey WO 96/04547, Parce et al. WO 98/46438 and Dubrow et al., WO 98/49548 (all of which are incorporated herein by reference in their entirety for all purposes), as well as in a variety of other references noted herein.

To provide appropriate electric fields, the system of the current microfluidic device optionally includes a voltage controller that is capable of applying selectable voltage levels, simultaneously, to, e.g., each of the various microchannels and micro-reservoirs. Such a voltage controller is optionally implemented using multiple voltage dividers and multiple relays to obtain the selectable voltage levels. Alternatively, multiple independent voltage sources are used. The voltage controller is electrically connected to each of the device's fluid conduits via an electrode positioned or fabricated within each of the plurality of fluid conduits (e.g., microchannels, microreservoirs, etc.). In one embodiment, multiple electrodes are positioned to provide for switching of the electric field direction in the, e.g., microchannel(s), thereby causing the analytes to travel a longer distance than the physical length of the microchannel. Use of electrokinetic transport to control material movement in interconnected channel structures was described in, e.g., WO 96/94547 to Ramsey. An exemplary controller is described in U.S. Pat. No. 5,800,690. Modulating voltages are concomitantly applied to the various fluid areas of the device to affect a desired fluid flow characteristic, e.g., continuous or discontinuous (e.g., a regularly pulsed field causing the sample to oscillate its direction of travel) flow of labeled components toward a waste reservoir. Particularly, modulation of the voltages applied at the various areas can move and direct fluid flow through the interconnected channel structure of the device.

The controlling instrumentation discussed above is also optionally used to provide for electrokinetic injection or withdrawal of fluidic material downstream of a region of interest to control an upstream flow rate. The same instrumentation and techniques described above are also utilized to inject a fluid into a downstream port to function as a flow control element.

The current invention also optionally includes other methods of fluid transport, e.g., available for situations in which electrokinetic methods are not desirable. See, above. For example, fluid transport and direction, etc. are optionally carried out in whole, or in part, in a pressure-based system to, e.g., avoid electrokinetic biasing during sample mixing. Additionally, as described above, pressure based fluid transport, or the like, is used in "regular" cross-sectional shaped microchannels (i.e., ones where the specific channel shape has not been configured to achieve a desired result such as keeping various fluidic materials together in a plug, or separation of fluidic materials, or the like) where, e.g., fluidic materials are to be separated without the use of, e.g., electrophoresis, separation matrices, etc. High throughput systems typically use pressure induced sample introduction. Pressure based flow is also desirable in systems in which electrokinetic transport is also used. For example, pressure based flow is optionally used for introducing and reacting reagents in a system in which the products are electrophoretically separated. In the present invention molecules are optionally loaded and other reagents are flowed through the microchannels or microreservoirs, etc. using, e.g., electrokinetic fluid control and/or under pressure.

Pressure is optionally applied to the microscale elements of the invention, e.g., to a microchannel, microreservoir, region, etc. to achieve fluid movement using any of a variety of techniques. Fluid flow and flow of materials suspended or solubilized within the fluid, including cells or molecules, is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, e.g., a plunger fitted into a material reservoir, for forcing material through a channel or other conduit, or is a combination of such forces. Internal sources include microfabricated pumps, e.g., diaphragm pumps, thermal pumps, lamb wave pumps and the like that have been described in the art. See, e.g., U.S. Pat. Nos. 5,271,724; 5,277,566; and 5,375,979 and Published PCT Application Nos. WO 94/05414 and WO 97/02347.

In some embodiments, a pressure source is applied to a reservoir or well at one end of a microchannel to force a fluidic material through the channel. Optionally, the pressure can be applied to multiple ports at channel termini, or, a single pressure source can be used at a main channel terminus. Optionally, the pressure source is a vacuum source applied at the downstream terminus of the main channel or at the termini of multiple channels. Pressure or vacuum sources are optionally supplied externally to the device or system, e.g., external vacuum or pressure pumps sealably fitted to the inlet or outlet of channels or to the surface openings of micro-reservoirs, or they are internal to the device, e.g., microfabricated pumps integrated into the device and operably linked to channels or they are both external and internal to the device. Examples of microfabricated pumps have been widely described in the art. See, e.g., published International Application No. WO 97/02357.

These applied pressures, or vacuums, generate pressure differentials across the lengths of channels to drive fluid flow through them. In the interconnected channel networks described herein, differential flow rates or volumes are optionally accomplished by applying different pressures or vacuums at multiple ports, or, by applying a single vacuum at a common waste port and configuring the various channels with appropriate resistance to yield desired flow rates. As discussed above, this is optionally done with multiple sources or by connecting a single source to a valve manifold comprising multiple electronically controlled valves, e.g., solenoid valves.

Hydrostatic, wicking and capillary forces are also optionally used to provide fluid flow of materials such as reagents, buffers, etc. in the invention. See, e.g., "METHOD AND APPARTUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In using wicking/capillary methods, an adsorbent material or branched capillary structure is placed in fluidic contact with a region where pressure is applied, thereby causing fluid to move towards the adsorbent material or branched capillary structure. Furthermore, the capillary forces are optionally used in conjunction with, e.g., electrokinetic or pressure-based flow in the channels, etc. of the present invention in order to pull fluidic material, etc. through the channels. Additionally, a wick is optionally added to draw fluid through a porous matrix fixed in a microscale channel or capillary. Use of a hydrostatic pressure differential is another optional way to control flow rates through the channels, etc. of the present invention. For example, in a simple passive aspect, a cell suspension is deposited in a reservoir or well at one end of a channel at sufficient volume or height so that the cell suspension creates a hydrostatic pressure differential along the length of the channel by virtue of, e.g., the cell suspension reservoir having greater height than a well at an opposite terminus of the channel. Typically, the reservoir volume is quite large in comparison to the volume or flow-through rate of the channel, e.g., 10 microliter reservoirs or larger as compared to a 100 micrometer channel cross section.

The present invention optionally includes mechanisms for reducing adsorption of materials during fluid-based flow, e.g., as are described in "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al., Ser. No. 09/310,027. In brief, adsorption of components, proteins, enzymes, markers and other materials to channel walls or other microscale components during pressure-based flow can be reduced by applying an electric field such as an alternating current to the material during flow. Alternatively, flow rate changes due to adsorption are detected and the flow rate is adjusted by a change in pressure or voltage.

The invention also optionally includes mechanisms for focusing labeling reagents, enzymes, modulators, and other components into the center of microscale flow paths, which is useful in increasing assay throughput by regularizing flow velocity, e.g., in pressure based flow, e.g., as are described in "FOCUSING OF MICROPARTICLES IN MICROFLUIDIC SYSTEMS" by H. Garrett Wada et al. Ser. No. 60/134,472, filed May 17, 1999. In brief, sample materials are focused into the center of a channel by forcing fluid flow from opposing side channels into the main channel, or by other fluid manipulation.

In an alternate embodiment, microfluidic systems of the invention can be incorporated into centrifuge rotor devices, which are spun in a centrifuge. Fluids and particles travel through the device due to gravitational and centripetal/centrifugal pressure forces.

Fluid flow or particle flow in the present devices and methods is optionally achieved using any one or more of the above techniques, alone or in combination. For example, electrokinetic transport can be used in one area or region of a microfluidic device in order to, e.g., move material through a microchannel whose cross-sectional geometry has been specifically configured to, e.g., keep various fluidic materials (e.g., cells and enzymes or the like) together in a plug. Additionally, pressure based flow could be used in a different region/area of the same microfluidic device where various fluidic materials (again, e.g., cells and enzymes or the like) are to be separated in a microchannel that has not been specifically configured to separate such materials (i.e., a "regularly" shaped microchannel). Myriad combinations of fluid transport methods can be combined in various embodiments of the present invention depending upon the specific needs of the system/assay being used. Typically, the controller systems involved are appropriately configured to receive or interface with a microfluidic device or system element as described herein. For example, the controller, optionally includes a stage upon which the device of the invention is mounted to facilitate appropriate interfacing between the controller and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

Detection

In general, detection systems in microfluidic devices include, e.g., optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more microchannels, microchambers, microreservoirs or conduits of the device, such that the detector is within sensory communication with the device, channel, reservoir, or chamber, etc. Detection systems can be used to, e.g., discern and/or monitor specific reactions, assays, etc. occurring within the microfluidic device, or alternatively, or additionally, to track, e.g., separation of fluidic materials and/or integrity of sample/component plugs (as occurring in the devices and methods of the current invention). The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Many different molecular/reaction characteristics can be detected in microfluidic devices of the current invention. For example, various embodiments can detect such things as fluorescence or emitted light, changes in the thermal parameters (e.g., heat capacity, etc.) involved in the assays, etc.

Examples of detection systems in the current invention can include, e.g., optical detection systems for detecting an optical property of a material within, e.g., the microchannels of the microfluidic devices that are incorporated into the microfluidic systems described herein. Such optical detection systems are typically placed adjacent to a microscale channel of a microfluidic device, and optionally are in sensory communication with the channel via an optical detection window or zone that is disposed across the channel or chamber of the device.

Optical detection systems of the invention include, e.g., systems that are capable of measuring the light emitted from material within the channel, the transmissivity or absorbance of the material, as well as the material's spectral characteristics, e.g., fluorescence, chemiluminescence, etc. Detectors optionally detect a labeled compound, such as fluorographic, colorimetric and radioactive components. Types of detectors optionally include spectrophotometers, photodiodes, avalanche photodiodes, microscopes, scintillation counters, cameras, diode arrays, imaging systems, photomultiplier tubes, CCD arrays, scanning detectors, galvo-scanners, film and the like, as well as combinations thereof. Proteins, antibodies, or other components which emit a detectable signal can be flowed past the detector, or alternatively, the detector can move relative to an array to determine molecule position (or, the detector can simultaneously monitor a number of spatial positions corresponding to channel regions, e.g., as in a CCD array). Examples of suitable detectors are widely available from a variety of commercial sources known to persons of skill See, also, *The Photonics Design and Application Handbook*, books 1, 2, 3 and 4, published annually by Laurin Publishing Co., Berkshire Common, P.O. Box 1146, Pittsfield, Mass. for common sources for optical components.

As noted above, the present devices optionally include, as microfluidic devices typically do, a detection window or zone at which a signal, e.g., fluorescence, is monitored. This detection window or zone optionally includes a transparent cover allowing visual or optical observation and detection of the assay results, e.g., observation of a colorimetric, fluorometric or radioactive response, or a change in the velocity of colorimetric, fluorometric or radioactive component.

Another optional embodiment of the present invention involves use of fluorescence correlation spectroscopy and/or confocal nanofluorimetric techniques to detect fluorescence from the molecules in the microfluidic device. Such techniques are easily available (e.g., from Evotec, Hamburg, Germany) and involve detection of fluorescence from molecules that diffuse through the illuminated focus area of a confocal lens. The length of any photon burst observed will correspond to the time spent in the confocal focus by the molecule. Various algorithms used for analysis can be used to evaluate fluorescence signals from individual molecules based on changes in, e.g., brightness, fluorescence lifetime, spectral shift, FRET, quenching characteristics, etc.

The sensor or detection portion of the devices and methods of the present invention can optionally comprise a number of different apparatuses. For example, fluorescence can be detected by, e.g., a photomultiplier tube, a charge coupled device (CCD) (or a CCD camera), a photodiode, or the like.

A photomultiplier tube is an optional aspect of the current invention. Photomultiplier tubes (PMTs) are devices which convert light (photons) into electronic signals. The detection of each photon by the PMT is amplified into a larger and more easily measurable pulse of electrons. PMTs are commonly used in many laboratory applications and settings and are well known to those in the art.

Another optional embodiment of the present invention comprises a charge coupled device. CCD cameras can detect even very small amounts of electromagnetic energy (e.g., such that emitted by fluorophores in the present invention). CCD cameras are made from semi-conducting silicon wafers that release free electrons when light photons strike the wafers. The output of electrons is linearly directly proportional to the amount of photons that strike the wafer. This allows the correlation between the image brightness and the actual brightness of the event observed. CCD cameras are very well suited for imaging of fluorescence emissions since they can detect even extremely faint events, can work over a broad range of spectrum, and can detect both very bright and very weak events. CCD cameras are well know to those in the art and several suitable examples include those made by: Stratagene (La Jolla, Calif.), Alpha-Innotech (San Leandro, Calif.), and Apogee Instruments (Tucson, Ariz.) among others.

Yet another optional embodiment of the present invention comprises use of a photodiode to detect fluorescence from molecules in the microfluidic device. Photodiodes absorb incident photons which cause electrons in the photodiode to diffuse across a region in the diode thus causing a measurable potential difference across the device. This potential can be measured and is directly related to the intensity of the incident light.

In some aspects, the detector measures an amount of light emitted from the material, such as a fluorescent or chemiluminescent material. As such, the detection system will typically include collection optics for gathering a light based signal transmitted through the detection window or zone, and transmitting that signal to an appropriate light detector.

Microscope objectives of varying power, field diameter, and focal length are readily utilized as at least a portion of this optical train. The detection system is typically coupled to a computer (described in greater detail below), via an analog to digital or digital to analog converter, for transmitting detected light data to the computer for analysis, storage and data manipulation.

In the case of fluorescent materials such as labeled cells or fluorescence indicator dyes or molecules, the detector optionally includes a light source which produces light at an appropriate wavelength for activating the fluorescent material, as well as optics for directing the light source to the material contained in the channel. The light source can be any number of light sources that provides an appropriate wavelength, including lasers, laser diodes and LEDs. Other light sources are optionally utilized for other detection systems. For example, broad band light sources for light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with a computer (described below), by permitting the use of few or a single communication port(s) for transmitting information between the controller, the detector and the computer. Integration of the detection system with a computer system typically includes software for converting detector signal information into assay result information, e.g., integrity of sample/component plugs comprising multiple fluidic materials; separation of fluidic materials, concentration of a substrate, concentration of a product, presence of a compound of interest, interaction between various samples, or the like.

Computer

As noted above, either, or both, the fluid direction system or the detection system, as well as other aspects of the current invention described herein (e.g., temperature control, etc.), are optionally coupled to an appropriately programmed processor or computer that functions to instruct the operation of these instruments in accordance with preprogrammed or user input instructions, receive data and information from these instruments, and interpret, manipulate and report this information to a user. As such, the computer is typically appropriately coupled to one or more of the appropriate instruments (e.g., including an analog to digital or digital to analog converter as needed).

The computer optionally includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of, e.g., the fluid direction and transport controller to carry out the desired operation.

For example, the computer is optionally used to direct a fluid direction system to control fluid flow, e.g., into and through a variety of interconnected microchannels (e.g., into and through the various microchannels of the invention, such as specially configured cross-sectional geometry areas and/or "regular" microchannel areas used for material separation, etc.). Additionally, the fluid direction system optionally directs fluid flow controlling which samples are contacted with each other and/or with various reagents, buffers, etc. in, e.g., a detection region or other region(s) in the microfluidic device. Furthermore, the fluid direction system optionally controls the coordination of movements of multiple fluids/molecules/etc. concurrently as well as sequentially. For example, the computer optionally directs the fluid direction system to direct the movement of at least a first member of a plurality of molecules into a first member of a plurality of microchannels concurrent with directing the movement of at least a second member of the plurality of molecules into one or more detection channel regions. Additionally or alternatively, the fluid direction system directs the movement of at least a first member of the plurality of molecules into the plurality of microchannels concurrent with incubating at least a second member of the plurality of molecules or directs movement of at least a first member of the plurality of molecules into the one or more detection channel regions concurrent with incubating at least a second member of the plurality of molecules.

By coordinating channel switching, the computer controlled fluid direction system directs the movement of at least one member of the plurality of molecules into the plurality of microchannels and/or one member into a detection region at a desired time interval, e.g., greater than 1 minute, about every 60 seconds or less, about every 30 seconds or less, about every 10 seconds or less, about every 1.0 seconds or less, or about every 0.1 seconds or less. Each sample, with appropriate channel switching as described above, remains in the plurality of channels for a desired period of time, e.g., between about 0.1 minutes or less and about 60 minutes or more. For example, the samples optionally remain in the channels for a selected incubation time of, e.g., 20 minutes.

The computer then optionally receives the data from the one or more sensors/detectors included within the system, interprets the data, and either provides it in a user understood format, or uses that data to initiate further controller instructions, in accordance with the programming, e.g., such as in monitoring and control of flow rates (e.g., as involved in separation of materials in "regular" microchannel areas or manipulation of dispersion rates and/or average velocity in specially configured microchannel areas, etc.), temperatures, applied voltages, pressures, and the like.

In the present invention, the computer typically includes software for the monitoring and control of materials in the various microchannels, etc. For example, the software directs channel switching to control and direct flow as described above. Additionally the software is optionally used to control electrokinetic, pressure-modulated, or the like, injection or withdrawal of material. The computer also typically provides instructions, e.g., to the controller or fluid direction system for switching flow between channels to help achieve a high throughput format.

In addition, the computer optionally includes software for deconvolution of the signal or signals from the detection system. For example, the deconvolution distinguishes between two detectably different spectral characteristics that were both detected, e.g., when a substrate and product comprise detectably different labels.

Any controller or computer optionally includes a monitor which is often a cathode ray tube ("CRT") display, a flat panel display (e.g., active matrix liquid crystal display, liquid crystal display), or the like. Data produced from the microfluidic device, e.g., fluorographic indication of separation of selected molecules, is optionally displayed in electronic form on the monitor. Additionally, the data gathered from the microfluidic device can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, interface circuits, etc. The box also optionally includes such things as a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

Exemplary Use of the Devices of the Present Invention

In a conventional bead-based immunoassay, the antibody molecules are covalently attached to beads. These bead bound antibody molecules are then exposed to target molecules. The mixture of the antibody/target complex and free target molecules are separated by washing following which a fluorescently labeled antibody conjugate is introduced and selectively bound to the complex. The excess label molecules are removed by a secondary washing step. Finally, the fluorescence signal from the labeled complex is measured for the detection of the amount of bound target.

The devices of the present invention simplify the above process by avoiding the need to have the two washing steps and helps to speed up the process significantly. For example, based on the configuration of the channel structure, the bound target and antibody complex will have a differential velocity from the free target molecules or in the case of the second wash step, the labeled antibody conjugate will have a differential velocity than the free flowing label resulting in a separation of the various species without having to introduce washing to actually cause the separation of the species. For example, as a plug of conjugate molecules is introduced and transported along a microfluidic channel to flow along a plug of beads, the two species will flow continuously down the microfluidic channel. The cross-sectional geometry of the channel can be configured in different regions of the channel such that the beads are initially flowing at the same speed as the free conjugate during incubation but flowing faster than the free conjugate after the reaction is completed. The differential velocity of the two species will than cause the two species to separate based on their mobility in the channel leaving one of the species behind and essentially separating the species without requiring an additional washing step.

Example Integrated System

Figure 4:
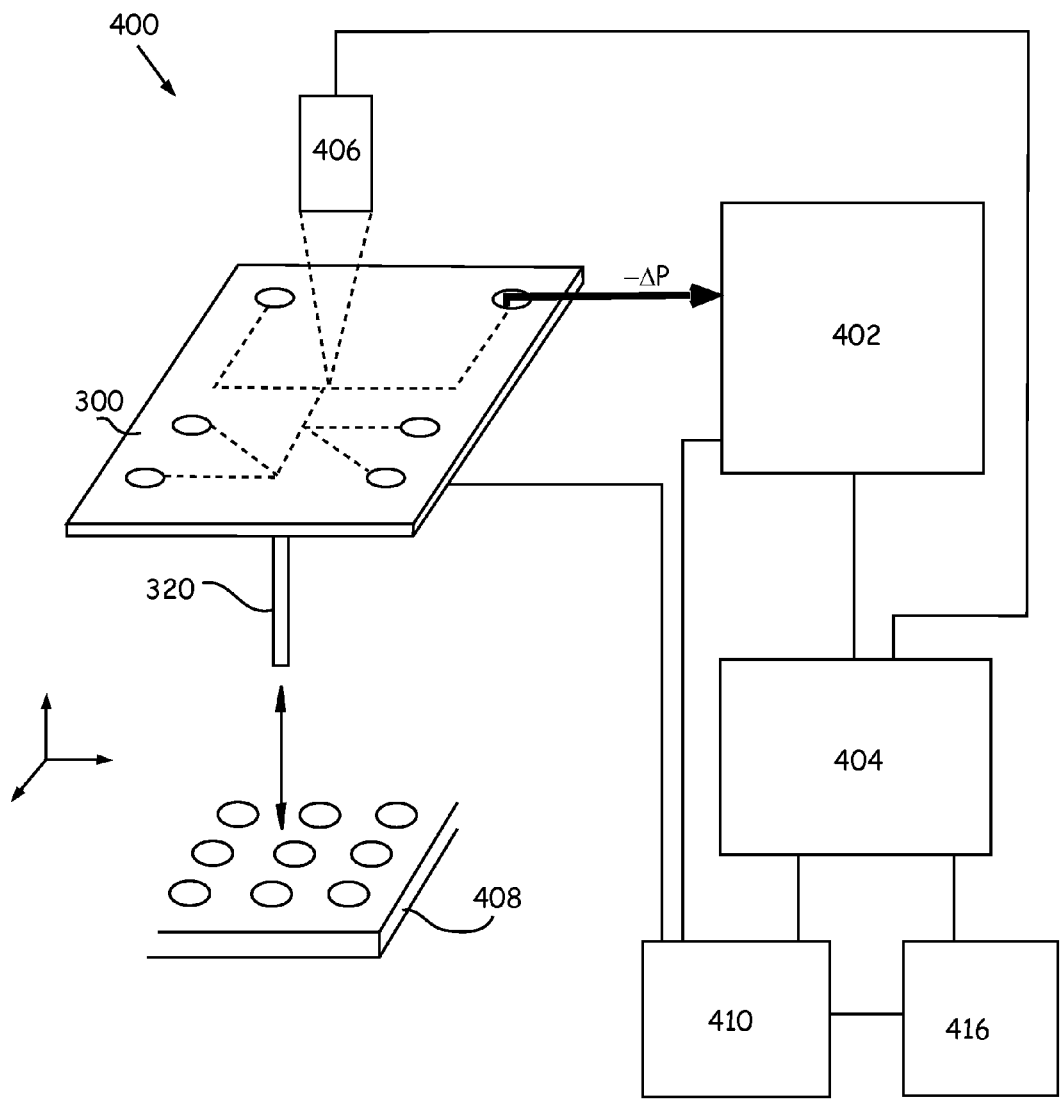
FIG. 4 is a schematic view of an integrated system comprising a microfluidic device incorporating the elements of the invention.

FIG. 3, Panels A, B, and C and FIG. 4 provide additional details regarding example integrated systems that optionally use the devices of the invention and optionally are used to practice the methods herein. As shown, body structure 302 has main channels 304 and 306 disposed therein. As stated previously, microchannels can comprise a number of areas comprising specifically configured cross-sectional geometry used to manipulate dispersion rates and/or average velocity (e.g., 304) additionally, numerous microchannels can comprise channels of "regular" cross-sectional geometry wherein fluidic materials are separated based on their differing dispersion rates and/or average velocity using non-electrokinetic flow (e.g., 306).

A sample or mixture of components, e.g., typically a buffer, sample, reagent, etc., is optionally flowed from pipettor channel 320 towards, e.g., reservoir 316, e.g., by applying a vacuum at reservoir 316 (or another point in the system) or by applying appropriate voltage gradients or wicking arrangements (or a combination of such forces). Alternatively, a vacuum, or appropriate pressure force, is applied at, e.g., reservoirs 308, 310 or through pipettor channel 320. Additional materials, such as buffer solutions, substrate solutions, enzyme solutions, test molecules, fluorescence indicator dyes or molecules and the like, are optionally flowed from wells, e.g., 308 or 310 and into channel 324 and thence into channel 304.

Alternatively, a sample or mixture of components, e.g., typically a buffer, sample, reagent, etc., is optionally flowed from pipettor channel 320 towards, e.g., reservoir 318 by any non-electrokinetic flow methods as described herein. Additional materials, such as buffer solutions, substrate solutions, enzyme solutions, test molecules, fluorescence indicator dyes or molecules and the like, are optionally flowed from wells, e.g., 308 or 310 and into channel 324 and thence into channel 306.

The arrangement of channels depicted in FIG. 3 is only one possible arrangement out of many which are appropriate and available for use in the present invention. For example, the number and arrangement of, e.g., microchannels comprising specifically configured cross-sectional geometry and/or "regular" microchannel regions used for material separation can all be altered depending upon the specific parameters of the assays to be performed, the need for high throughput analysis, etc. Additional alternatives can be readily devised, e.g., by combining the microfluidic elements described herein with other microfluidic devices described in the patents and applications referenced herein.

Samples and materials are optionally flowed from the enumerated wells or from a source external to the body structure. As depicted, the integrated system optionally includes pipettor channel 320, e.g., protruding from body 302, for accessing a source of materials external to the microfluidic system. Typically, the external source is a microtiter dish or other convenient storage medium. For example, as depicted in FIG. 4, pipettor channel 320 can access microwell plate 408, which, in the wells of the plate, optionally includes, e.g., samples, buffers, fluorescence dyes, various fluidic reagents to be interacted with the samples, etc.

Detector 406 is in sensory communication with, e.g., specifically configured cross-sectional geometry microchannel 304 and/or "regular" cross-sectional geometry channel 306, detecting signals resulting, e.g., from labeled materials flowing through the detection region, changes in thermal parameters, fluorescence, etc. Detector 406 is optionally coupled to any of the channels or regions of the device where detection is desired. Detector 406 is operably linked to computer 404, which digitizes, stores, and manipulates signal information detected by detector 406, e.g., using any of the instructions described above or any other instruction set, e.g., for determining concentration, molecular weight or identity, interaction between samples and test molecules, separation of fluidic materials, integrity of sample/component plugs, or the like.

Fluid direction system 402 controls voltage, pressure, etc. (or a combination of such), e.g., at the wells of the systems or through the channels of the system, or at vacuum couplings fluidly coupled to main channel 304, 306, or any other channel described above. Optionally, as depicted, computer 404 controls fluid direction system 402. In one set of embodiments, computer 404 uses signal information to select further parameters for the microfluidic system. For example, upon detecting the interaction between a particular sample and a first reagent, the computer optionally directs addition of a second reagent of interest into the system to be tested against that particular sample.

Temperature control system 410 controls joule and/or non-joule heating at, e.g., the wells of the systems or through the channels of the system as described herein. Optionally, as depicted, computer 404 controls temperature control system 410. In one set of embodiments, computer 404 uses signal information to select further parameters for the microfluidic system. For example, upon detecting the desired temperature in a sample in, e.g., channel 304, the computer optionally directs addition of, e.g., a potential binding molecule, fluorescence indicator dye, etc. into the system to be tested against one or more samples.

Monitor 416 displays the data produced by the microfluidic device, e.g., graphical representation of, e.g., separation or non-separation of fluidic materials, interaction (if any) between samples, reagents, test molecules, etc. Optionally, as depicted, computer 404 controls monitor 416. Additionally, computer 404 is connected to and directs additional components such as printers, electronic data storage devices and the like.

Assay Kits

The present invention also provides kits for utilizing the microfluidic devices of the invention. In particular, these kits typically include microfluidic devices, systems, modules and workstations, etc. A kit optionally contains additional components for the assembly and/or operation of a multimodule workstation of the invention including, but not restricted to robotic elements (e.g., a track robot, a robotic armature, or the like), plate handling devices, fluid handling devices, and computers (including e.g., input devices, monitors, c.p.u., and the like).

Generally, the microfluidic devices described herein are optionally packaged to include some or all reagents for performing the device's functions. For example, the kits can optionally include any of the microfluidic devices described along with assay components, buffers, reagents, enzymes, serum proteins, receptors, sample materials, antibodies, substrates, control material, spacers, buffers, immiscible fluids, etc., for performing the assays, separations, dispersion rate and/or average velocity manipulations, etc. using the methods/devices of the invention. In the case of prepackaged reagents, the kits optionally include pre-measured or pre-dosed reagents that are ready to incorporate into the assays without measurement, e.g., pre-measured fluid aliquots, or pre-weighed or pre-measured solid reagents that can be easily reconstituted by the end-user of the kit.

Such kits also typically include appropriate instructions for using the devices and reagents, and in cases where reagents (or all necessary reagents) are not predisposed in the devices themselves, with appropriate instructions for introducing the reagents into the channels/chambers/reservoirs/etc. of the device. In this latter case, these kits optionally include special ancillary devices for introducing materials into the microfluidic systems, e.g., appropriately configured syringes/pumps, or the like (in one embodiment, the device itself comprises a pipettor element, such as an electropipettor for introducing material into channels/chambers/reservoirs/etc. within the device). In the former case, such kits typically include a microfluidic device with necessary reagents predisposed in the channels/chambers/reservoirs/etc. of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (e.g., enzymatic inhibitors, microbicides/bacteriostats, anticoagulants, etc.), the physical stabilization of the material, e.g., through immobilization on a solid support, entrapment in a matrix (e.g., a bead, a gel, etc.), lyophilization, or the like.

The elements of the kits of the present invention are typically packaged together in a single package or set of related packages. The package optionally includes written instructions for utilizing one or more device of the invention in accordance with the methods described herein. Kits also optionally include packaging materials or containers for holding the microfluidic device, system or reagent elements.

The discussion above is generally applicable to the aspects and embodiments of the invention described herein. Moreover, modifications are optionally made to the methods and devices described herein without departing from the spirit and scope of the invention as claimed, and the invention is optionally put to a number of different uses including the following:

The use of a microfluidic system containing at least a first substrate and having a first channel and a second channel intersecting the first channel, at least one of the channels having at least one cross-sectional dimension in a range from 0.1 to 500 micrometer, in order to test the effect of each of a plurality of test compounds on a biochemical system comprising one or more focused cells or particles.

The use of a microfluidic system as described herein, wherein a biochemical system flows through one of said channels substantially continuously, providing for, e.g., sequential testing of a plurality of test compounds.

The use of a microfluidic device as described herein to modulate reactions within microchannels/microchambers/reservoirs/etc.

The use of electrokinetic injection in a microfluidic device as described herein to modulate or achieve flow in the channels.

The use of a combination of wicks, electrokinetic injection and pressure based flow elements in a microfluidic device as described herein to modulate, focus, or achieve flow of materials, e.g., in the channels of the device.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of enhancing a dispersion of at least one of at least two materials in a fluidic device, the method comprising flowing a first material having a first dispersion rate and a second material having a second dispersion rate through a channel of a fluidic device, wherein a cross-sectional geometry of at least a first region of the channel is shaped and dimensioned so as to cause the first dispersion rate to be at least 1.25 times or more greater than the second dispersion rate, and wherein flowing does not comprise electrokinetic flow.

2. The method of claim 1, wherein the first region has a cross-sectional geometry that comprises a center segment and first and second side segments, each of the side segments having a first maximum depth, the center segment having a second maximum depth-greater than the first maximum depth, and wherein a wall of the first region has a substantially perpendicular transition where the first side segment abuts the center segment.

3. The method of claim 2, wherein the first dispersion rate is enhanced relative to the second dispersion rate such that the first and second materials have substantially the same average velocity.

4. The method of claim 2, wherein the first dispersion rate is governed by convection and molecular diffusion, and wherein the second dispersion rate is governed by convection alone.

5. The method of claim 2, wherein the fluidic device comprises a first substrate bonded to a second substrate, and wherein the channel region is formed into a surface of at least one of the two substrates, the first substrate and the second substrate being joined such that the channel region is defined by the interface of the two substrates.

6. The method of claim 5, wherein a first portion of the channel region is formed into a surface of the first substrate and a second portion of the channel region is formed into a surface of the second substrate.

7. The method of claim 6, wherein the first portion is narrower in width than the second portion, and wherein the substrates are bonded such that the first portion is substantially centered laterally over the second portion.

8. The method of claim 6, wherein the width of the first portion is substantially the same as the width of the second portion, and wherein the substrates are bonded such that the first portion is offset laterally from the second portion, the first portion partially overlapping the second portion, the overlap of the two portions forming the center segment of the channel region cross-sectional geometry.

9. The method of claim 1, wherein the first region has a cross-sectional geometry that comprises a center segment and first and second side segments, each of the side segments having a first maximum depth, the center segment having a second maximum depth-less than the first maximum depth, and wherein a wall of the first region has a substantially perpendicular transition where the first side segment abuts the center segment.

10. The method of claim 9, wherein the first dispersion rate is enhanced relative to the second dispersion rate such that a difference in velocity between the first and second materials is enhanced.

11. The method of claim 10, wherein the first dispersion rate is governed by convection alone, and wherein the second dispersion rate is governed by convection and molecular diffusion.

12. The method of claim 9, wherein the fluidic device comprises a first substrate bonded to a second substrate, the first substrate and the second substrate being joined such that the channel region is defined by the interface of the two substrates, wherein the microchannel region is formed into a surface of at least one of the two substrates.

13. The method of claim 12, wherein a first portion of the microchannel region is formed into a surface of the first substrate and a second portion of the microchannel region is formed into a surface of the second substrate, and wherein the cross-sectional geometry of the first portion is substantially the same as the cross-sectional geometry of the second portion, each portion comprising a center section and two side sections, the center section of each portion having a maximum depth less than that of the side sections.

14. The method of claim 1, wherein the channel does not comprise a separation matrix.

15. The method of claim 1, wherein the cross-sectional geometry of the first region of the at least one channel is shaped and dimensioned to cause the first dispersion rate to be at least 5 times or more greater than the second dispersion rate.

16. The method of claim 1, wherein the cross-sectional geometry of the first region of the at least one channel is shaped and dimensioned to cause the first dispersion rate to be at least 10 times or more greater than the second dispersion rate.

17. The method of claim 1, wherein flowing comprises one or more of positive pressure flow, negative pressure flow, hydrostatic pressure flow, or wicking forces flow.

* * * * *